United States Patent
Chen et al.

(10) Patent No.: US 11,992,483 B2
(45) Date of Patent: May 28, 2024

(54) EMULSIONS FOR LOCAL ANESTHETICS

(71) Applicant: Cali Pharmaceuticals, LLC, San Diego, CA (US)

(72) Inventors: Andrew Xian Chen, San Diego, CA (US); Lijia Chen, San Diego, CA (US); Damian McLoud, San Diego, CA (US)

(73) Assignee: CALI BIOSCIENCES US, LLC, San Diego, CA (US)

(*) Notice: Subject to any disclaimer, the term of this patent is extended or adjusted under 35 U.S.C. 154(b) by 58 days.

(21) Appl. No.: 17/369,369

(22) Filed: Jul. 7, 2021

(65) Prior Publication Data
US 2022/0313669 A1 Oct. 6, 2022

Related U.S. Application Data

(60) Provisional application No. 63/169,121, filed on Mar. 31, 2021.

(51) Int. Cl.
| | | |
|---|---|---|
| *A61K 31/445* | (2006.01) | |
| *A61K 9/00* | (2006.01) | |
| *A61K 9/107* | (2006.01) | |
| *A61K 31/167* | (2006.01) | |
| *A61K 31/381* | (2006.01) | |
| *A61K 31/47* | (2006.01) | |
| *A61K 47/24* | (2006.01) | |
| *A61K 47/44* | (2017.01) | |
| *A61P 17/02* | (2006.01) | |
| *A61P 23/02* | (2006.01) | |

(52) U.S. Cl.
CPC .......... *A61K 31/445* (2013.01); *A61K 9/0019* (2013.01); *A61K 9/107* (2013.01); *A61K 31/167* (2013.01); *A61K 31/381* (2013.01); *A61K 31/47* (2013.01); *A61K 47/24* (2013.01); *A61K 47/44* (2013.01); *A61P 17/02* (2018.01); *A61P 23/02* (2018.01)

(58) Field of Classification Search
CPC .... A61K 31/445; A61K 9/107; A61K 31/167; A61P 23/02
See application file for complete search history.

(56) References Cited

U.S. PATENT DOCUMENTS

| | | |
|---|---|---|
| 5,091,188 A | 2/1992 | Haynes |
| 5,188,837 A | 2/1993 | Domb |
| 5,693,337 A | 12/1997 | Suzuki et al. |
| 6,100,302 A | 8/2000 | Pejaver et al. |
| 6,147,122 A | 11/2000 | Mirejovsky et al. |
| 6,464,987 B1 | 10/2002 | Fanara et al. |
| 6,471,970 B1 | 10/2002 | Fanara et al. |
| 6,818,224 B2 | 11/2004 | Fanara et al. |
| 7,261,903 B1 | 8/2007 | Weinberg et al. |
| 7,476,400 B2 | 1/2009 | Patel |
| 7,713,440 B2 | 5/2010 | Anderson |
| 8,449,863 B2 | 5/2013 | Anderson |
| 9,072,656 B2 | 7/2015 | Desai et al. |
| 9,517,202 B2 | 12/2016 | Chen et al. |
| 9,668,974 B2 | 6/2017 | Amselem et al. |
| 9,763,892 B2 | 9/2017 | Trieu et al. |
| 9,849,088 B2 | 12/2017 | Amselem et al. |
| 10,206,876 B2 | 2/2019 | Amselem et al. |
| 10,426,727 B2 | 10/2019 | Mecozzi et al. |
| 2007/0207173 A1 | 9/2007 | Chen |
| 2015/0045403 A1 | 2/2015 | Shanler et al. |
| 2016/0310715 A1* | 10/2016 | Lee ..................... A61M 31/002 |
| 2017/0049789 A1 | 2/2017 | Bhalani et al. |
| 2017/0290781 A1 | 10/2017 | Mo et al. |
| 2018/0235882 A1 | 8/2018 | Sheikh et al. |
| 2018/0296506 A1 | 10/2018 | Campbell et al. |
| 2020/0069583 A1 | 3/2020 | Gong et al. |
| 2022/0046941 A1 | 2/2022 | Brahms et al. |
| 2022/0193014 A1 | 6/2022 | Zhang et al. |
| 2022/0218611 A1 | 7/2022 | Foldvari |
| 2023/0080811 A1 | 3/2023 | Gan et al. |

FOREIGN PATENT DOCUMENTS

| | | | |
|---|---|---|---|
| CN | 102370619 | * | 3/2012 |
| CN | 102370619 A | | 3/2012 |
| CN | 102526753 A | | 7/2012 |
| WO | 9939696 A1 | | 8/1999 |
| WO | 9956726 A1 | | 11/1999 |
| WO | 0003660 A1 | | 1/2000 |
| WO | 0059471 A1 | | 10/2000 |
| WO | 03105817 A1 | | 12/2003 |
| WO | 2005067905 A1 | | 7/2005 |
| WO | 2005077337 A2 | | 8/2005 |
| WO | 2006002050 A1 | | 1/2006 |
| WO | 2006003481 A2 | | 1/2006 |
| WO | 2006112276 A1 | | 10/2006 |
| WO | 2006128088 A1 | | 11/2006 |

(Continued)

OTHER PUBLICATIONS

Zink et. al. (Drug Safety (2004) 27:1093-1114). (Year: 2004).*
Simpson et. al. (Drugs (2006) 65:2675-2717). (Year: 2006).*
Golzari et. al. (Anesth. Pain Med. (2014) 1-6). (Year: 2014).*
Yousefshahi et. al. (Anesth. Pain Med. (2017) 1-7). (Year: 2017).*
International Application No. PCT/US2022/021721, International Search Report and Written Opinion dated Jun. 16, 2022, 9 pages.

*Primary Examiner* — Marcos L Sznaidman

(74) *Attorney, Agent, or Firm* — Kilpatrick Townsend & Stockton LLP

(57) ABSTRACT

Use of an emulsion for pain relief comprising a local anesthetic, lecithin, oil and an aqueous phase, wherein local anesthetic is non-covalent bound to the emulsion oil droplets and the emulsion is physically and chemically stable and said emulsion provides better safety, extended release pharmacokinetics and a prolonged duration of action of the local anesthetic.

26 Claims, 6 Drawing Sheets

(56) References Cited

FOREIGN PATENT DOCUMENTS

| | | | |
|---|---|---|---|
| WO | 2007000662 | A2 | 1/2007 |
| WO | WO 2007/089931 | * | 8/2007 |
| WO | 2007102052 | A2 | 9/2007 |
| WO | 2007124465 | A2 | 11/2007 |
| WO | 2008000534 | A1 | 1/2008 |
| WO | 2010012408 | A2 | 2/2010 |
| WO | 2010082092 | A1 | 7/2010 |
| WO | 2010129278 | A1 | 11/2010 |
| WO | 2010139278 | A1 | 12/2010 |
| WO | 2014147255 | A1 | 9/2014 |
| WO | 2016196648 | A1 | 12/2016 |
| WO | 2017218630 | A2 | 12/2017 |
| WO | 2018013595 | A1 | 1/2018 |
| WO | 2020211762 | A1 | 10/2020 |
| WO | 2021129635 | A1 | 7/2021 |
| WO | 2021247774 | A1 | 12/2021 |
| WO | 2022082082 | A2 | 4/2022 |
| WO | 2022152232 | A1 | 7/2022 |
| WO | 2022182655 | A2 | 9/2022 |
| WO | 2022186802 | A1 | 9/2022 |
| WO | 2022195521 | A1 | 9/2022 |
| WO | 2022207580 | A2 | 10/2022 |
| WO | 2022212166 | A1 | 10/2022 |
| WO | 2022217147 | A1 | 10/2022 |

* cited by examiner

Undiluted emulsion sample under TEM

Diluted emulsion sample under TEM

Liposome particles with bilayer membranes of Ambisome under TEM

EMULSIONS FOR LOCAL ANESTHETICS

CROSS-REFERENCES TO RELATED APPLICATIONS

This application claims priority to U.S. Provisional Patent Application No. 63/169,121, filed Mar. 31, 2021, the contents of which are hereby incorporated by reference in their entirety for all purposes.

FIELD OF THE DISCLOSURE

This disclosure relates to use of pharmacologically active, safe and long-acting emulsions containing a local anesthetic.

BACKGROUND

Local anesthetic drugs (LA), such as lidocaine, bupivacaine, prilocaine, levobupivacaine and ropivacaine, are chemically related amide local anesthetics and share the same mechanism of action by inhibiting voltage-gated sodium channels, which slows membrane depolarization and repolarization and results in membrane stabilization (See, Daniel E. Becker and Kenneth L. Reed, Local Anesthetics: Pharmacological Considerations, Anesth Prog 59:90, 102 2012).

Local anesthetics have been shown to be effective and are used widely in preventing or reducing pain from minor surgery, incisions, biopsies, dental and obstetrical procedures and pain from wounds.

Local anesthetics are usually given as a single injection locally into a lesion or the area of incision and their anesthetic activities last about a few hours owing to their short half-lives (up to about 4 hr). For a longer action, a slow and continuous infusion to the affected tissue can be applied by epidural or wound-delivering catheters for several days. This long infusion is inconvenient to administer and a single injection of a slow-release formulation to provide prolonged action for a LA is highly desirable.

Various methods have been developed to extend LA duration of action including
1. Embedding LA in liposomal vesicles to slow down its release (See, U.S. Pat. Nos. 8,182,835 and 10,206,876)
2. Incorporating LA in a polymer matrix for slow release. (See, U.S. Pat. No. 10,898,575).
3. Co-administering LA with the vessel restrictor epinephrine (See, Lixtraxen Injection (Lidocaine hydrochloride and epinephrine injection, solution) https://www.drug.com/pro/lixtraxen-injection.html.

Emulsions have been used to deactivate a LA or as an antidote for LA overdose. It is also well documented that an emulsion that contains no drug is commonly used to decrease the cardiovascular effect or toxicity of a LA. Various researchers have clearly demonstrated that emulsions can deactivate LA, resulting in loss of the LA's pharmacological effect and toxicity (See, Zausig, York A. et al., Lipid Emulsion Improves Recovery from Bupivacaine-Induced Cardiac Arrest, but Not from Ropivacaine- or Mepivacaine-Induced Cardiac Arrest, Anesthesia & Analgesia: October 2009—Volume 109—Issue 4—p 1323-1326; E. Litonius, et al, Effect of intravenous lipid emulsion on bupivacaine plasma concentration in humans, Anaesthesia 2012, 67, 600-605; Lotte C. G. et al, Systematic review of the effect of intravenous lipid emulsion therapy for local anesthetic toxicity, Clinical Toxicology, 2016 Vol. 54, No. 3, 167-193, http://dx.doi.org/10.3109/15563650.2015.1121 270). Using an emulsion to deliver a pharmacologically active LA is against the common understanding and medical practice.

This application relates to a surprising finding that, in contrary to the current understanding and medical practice of using emulsions to deactivate LAs, this application discloses the use of the emulsions to not only maintain the pharmacological effect of an LA but also prolong its duration of action and reduce its toxicity. The emulsions of this invention are particularly useful for managing the surgery or trauma-related pain as the emulsions of this invention can prolong LA activity for 1-5 days after a single injection thus providing an extended pain relief benefit.

BRIEF SUMMARY

This invention relates to use of LA-containing emulsion compositions that
  a. Maintain and extend pharmacological activity for the LA (Ex 2)
  b. Are safer than solutions containing the same LA (Ex 3)
  c. Provide extended pharmacokinetic profile vs. the free LA in solution (Ex 1)
  d. Provide a prolonged anesthetic action for up to about 1-3 days (Ex 1 & 2)

As such, the present invention teaches use of an emulsion compositions, comprising, consisting essentially of, or consisting of:
  a) a local anesthetic,
  b) an oil phase, and
  c) an aqueous phase
wherein
  i. the local anesthetic is at a concentration up to 4% by weight of the emulsion,
  ii. the oil phase comprises lecithin and vegetable oil at weight ratio between 2:1 and 1:2,
  iii. the oil phase is at a concentration between about 33% and 99.5% by weight of the emulsion, and
  iv. the emulsion contains particles or droplets with a diameter between about 30 to about 2500 nanometers.

In one embodiment, the emulsion of this invention contains a LA selected from the group consist of lidocaine, bupivacaine, and ropivacaine (Ex 2).

In one embodiment, the emulsion of this invention contains a LA free base or a pharmaceutically acceptable salt such as hydrochloride salt (Ex 3).

In one embodiment, the emulsion of this invention is injectable liquid (Ex 11).

In one embodiment, the emulsion of this invention has particles or oil droplets of size between about 30 to about 2500 nanometers in diameter, the range is selected because less than 30 nm can result in a compromised extended-release profile (i.e., release too fast), and more than 2500 nm can result in a very viscous liquid that is difficult for injection (Ex 9, 10).

In one embodiment, the emulsion of this invention has particles or oil droplets with an average diameter of at between about 200 nm and 2500 nm (Ex 9).

In one embodiment, the emulsion of this invention has particles of smaller than 100 nm and particles larger than 100 nm in diameter.

In one embodiment, the emulsion of this invention has particles that are polydisperse in size with a polydispersity index (PDI) >0.7 (Ex 17).

In one embodiment, the emulsion of this invention has particles with a PDI above 0.7, preferably above 0.8 and most preferable above 0.9. (Ex 17).

In one embodiment, the emulsion of this invention has non-liposomal particles with solid cores and absence of detectable lipid bilayer membrane surrounding the particle (Ex 10).

In one embodiment, the emulsion of this invention is formed after being diluted or mixed with water (Ex 9).

In one embodiment, the oil phase is present in the emulsion at a concentration of about between 33% and 99.5% of the weight of the emulsion (Ex 12 & 13).

In one embodiment, the oil phase comprises a lecithin, oil and LA.

In one embodiment, the lecithin is present in the oil phase at a concentration of about between 55% and 67% of the weight of the oil phase.

In one embodiment, the oil is present in the oil phase at a concentration of about between 33% and 44% of the weight of the oil phase, the ratio is preferred because too much lecithin can make the emulsion too viscous to inject through a needle, whereas too much oil cannot adequately solubilize LA since oil itself is not a good solvent for LA nor provide the prolonged release for LA.

In one embodiment, the lecithin and oil are present in the oil phase at a weight ratio between 2:1 and 5:4.

In one embodiment, the emulsion of this invention contains up to 4% LA by weight of the emulsion.

In one embodiment, more than 90% by weight of the LA is distributed or partitioned in the oil phase of the emulsion.

In one embodiment, the emulsion of this invention is translucent or opaque liquid having a viscosity ranging from about 300 to 600 cps (Ex 8).

In one embodiment, no less than 90% of the LA in the emulsion of this invention is bound to the emulsion oil phase regardless of the hydrophobicity of the LA (Ex 3).

In one embodiment, the emulsion of this invention provides a similar LA activity for a LA freebase and its salt (Ex 3).

In one embodiment, no less than 90% of the LA in the emulsion of this invention is bound to the emulsion oil phase even if the LA is not hydrophobic or having a log P value less than 1.5.

In one embodiment, the emulsion of this invention contains a hydrophobic and water-insoluble LA such as the free base (un-ionized) form of lidocaine, bupivacaine or ropivacaine.

In a preferred embodiment, the emulsion of this invention contains non-hydrophobic or water-soluble LA in an ionized form such as a hydrochloride salt of ropivacaine, bupivacaine or lidocaine.

In one embodiment, the oil droplets of the emulsion of this invention is substantially free of the lipid bilayer membrane which is the essential structural feature of liposome vesicles. (Ex 10).

In one embodiment, the emulsion of this invention is free of a polymer.

In one embodiment, the emulsion of this invention releases LA slowly (Ex 7, 13) such as over 1, 2, 3 or 4 days of release and efficacy.

In one embodiment, the emulsion of this invention releases LA at a different rate from a pre-liposome composition containing the same LA (Ex 7).

In one embodiment, the emulsion of this invention is not bioequivalent to a pre-liposome composition containing the same LA.

In one embodiment, the emulsion of this invention does not have any organic solvent such as alcohol.

In another embodiment, the emulsion of this invention may have an organic solvent that is miscible with water.

In one embodiment, the emulsion of this invention can be injected through an 18-27G needle or 22G catheter with a 10 mL syringe (Ex 11).

In one embodiment, the emulsion of this invention comprises an aqueous phase and an oil phase, wherein the oil phase comprises LA, a vegetable oil, and a lecithin derived from egg or soybean.

In another embodiment, the emulsion of this invention has a pH between pH 3 and pH 8.

In one embodiment, the emulsion composition of this invention does not contain any synthetic surfactant or polymer.

In one embodiment, the emulsion of this invention is ready-to-use or ready-for-injection.

In another embodiment, the emulsion of this invention is mixed with water or an aqueous solution such as saline before injection.

In one embodiment, the emulsion is a water-in-oil emulsion. In another embodiment, the emulsion is an oil-in-water emulsion. In another embodiment, diluting the water-in-oil emulsion with diluent such as water, saline converts it into oil-in-water emulsion. In certain other embodiments, removing excess water from an oil-in-water emulsion by for example, vacuum drying, will generate a water-in-oil emulsion, oil-in-water emulsion, or an emulsion of both oil-in-water and water-in-oil types.

In one embodiment, the emulsion of this invention is physically stable and does not form LA precipitates, undergo phase separation and change in appearance after being stored at 25° C. for 2 years (Ex 8).

In one embodiment, the emulsion of this invention is chemically stable and retains no less than 95% of the intact LA after being stored at 25° C. for 2 years. (Ex 8)

In one embodiment, the emulsion of this invention contains less than 0.2% of the N-oxide of the LA after being stored at 25° C. for 2 years (Ex 8).

In another embodiment, the emulsion of this invention may optionally contain an antioxidant selected from a group comprising methionine, cysteine, dextrose, fructose, lactose, and a salt of edetate (EDTA).

In one embodiment, the emulsion of this invention contains a combination of EDTA sodium and cysteine (Ex 16)

In one embodiment, the emulsion of this invention is for administration via infiltration or injection onto a wound surface, surgical incision or into a soft tissue.

In one embodiment, the emulsion of this invention provides a prolonged PK profile for an LA compared to a solution formulation of the same LA following injection into a soft tissue (Ex 1).

In one embodiment, the emulsion of this invention provides a long action in inhibiting pain (Ex 2).

In one embodiment, the emulsion of this invention is safer than a solution formulation of the same LA (Ex 4).

In one embodiment, the invention provides a method for preventing or treating pain comprising administering to a patient with an emulsion of this invention.

In some embodiments, the emulsion of this invention is administered as a single dose, i.e., only once for the entire treatment.

In some embodiments, the emulsion of this invention is administered for multiple times, i.e., more than once during the cause of the treatment.

In some embodiments, the emulsion of this invention is administered as is, i.e., undiluted.

In some embodiments, the emulsion of this invention is administered after it is diluted in water or another liquid that is safe for administration in human.

In some embodiments, the emulsion of this invention is administered into a tissue near the site of the pain, such as a surgical incision or a trauma wound.

In some embodiments, the emulsion of this invention is administered to an incision of a surgery including, but not limited to, an incision of a soft-tissue surgery, including, but not limited to, general surgery, performed either via open technique or laparoscopic technique; abdominal surgeries including, but not limited to, gastrectomy, proctocolectomy, appendectomy, pancreatectomy, cholecystectomy, herniorrhaphy; colorectal surgeries, such as colectomy, ileostomy, APR, and hemorrhoidectomy; thoracic surgeries such as pneumonectomy, esophagectomy; hepatic surgery such as liver cancer surgery; plastic surgery such as abdominoplasty, breast augmentation or mastopexy; urologic surgery such as prostatectomy or cystectomy; obstetrics and gynecology surgeries, including myomectomy, sterilization, hysterectomy, and TAHBSO; and ear-nose-throat surgeries. In some embodiments, the emulsion of this invention is also administered to an incision of a bony-tissue surgery, including, but not limited to, orthopedic surgeries, such as hop and knee arthroplasty, open reduction and internal fixation of fractures and joints, laminectomy and spinal fusion; thoracic surgeries such as sternal incision and pectus excavatum repair; podiatric surgery including bunionectomy; and general bony surgeries including iliac crest grafts.

In some embodiments, the emulsion of this invention is administered to trauma wound including, but not limited to, abrasions, lacerations, skin tears, bites, burns and penetrating trauma wounds.

In some embodiments, the emulsion of this invention is administered to a surgical incision, or a trauma wound at an LA concentration between 0.5% and 4%, preferably between 1% and 3% and most preferably between 1.5% and 2.5%.

In some embodiments, the emulsion of this invention is administered by infiltration or injection into a soft tissue at or near the surgical site, pain site or nerve.

In some embodiments, the emulsion of this invention is administered by infiltration or injection into an incision site in a soft-tissue or bony-tissue surgery.

In some embodiments, the emulsion of this invention is administered by instillation or topical application onto the surgical incision or wound site.

In some embodiments, the emulsion of this invention is administered by instillation or topical application onto a soft or bony-tissue.

In some embodiments, the emulsion of this invention is administered by both infiltration and instillation.

In some embodiments, the emulsion of this invention is administered by instillation at a volume up to 5, 10, 15, 20, 25, 30, 40 or 50 mL per surgical incision or wound site.

In some embodiments, the emulsion of this invention is administered by instillation at a volume up to 30 mL, preferably 25 mL or more preferably 20 mL per surgical incision or wound site.

In some embodiments, the emulsion of this invention is administered by infiltration at a volume up to 5, 10, 15, 20, 25, 30, 40 or 50 mL per surgical incision or wound site.

In some embodiments, the emulsion of this invention is administered by infiltration at a volume up to 1, 2, 3, 4, 5, 6, 7, 8, 9, 10, 11, 12, 13, 14, 15, 16, 17, 18, 19, 20, 25, 30, 40 and 50 mL per surgical incision or wound site.

In some embodiments, the emulsion of this invention is administered by both instillation and infiltration with a total up to 10, 15, 20, 25, 30, 40 and 50 mL per surgical incision or wound site.

In some embodiments, the emulsion of this invention is administered by instillation and infiltration at a volume ratio between 1:20 and 20:1.

In some embodiments, the emulsion of this invention is administered by instillation and infiltration to a surgical incision before, during and after the surgery.

In some embodiments, the emulsion of this invention is administered by instillation and infiltration to a surgical incision before the closure of incision by suture.

In some embodiments, the emulsion of this invention is administered by injection or infiltration into, onto or surrounding the soft tissue or bony tissue including, but not limited to, bone, joint, fascia, muscle, fat, subcutaneous tissues, skin tissues in the incision before the closure of incision by suture.

In some embodiments, the emulsion of this invention is administered by instillation into, onto or surrounding to the soft tissue or bony tissue including, but not limited to, bone, joint, fascia, muscle, fat, subcutaneous tissues, skin tissues in the incision before the closure of incision by suture.

In some embodiments, the emulsion of this invention is administered by intramuscular, intra-articular, peri-articular, subcutaneous injection or percutaneous injection into, onto or surrounding to the soft tissue or bony tissue including, but not limited to, bone, joint, fascia, muscle, fat, subcutaneous tissues, skin tissues at or surrounding the incision after closure of the incision.

In some embodiments, the emulsion of this invention is administered by topical application onto a closed incision or wound.

In some embodiments, the emulsion of this invention is administered by infiltration using a syringe attached with a needle.

In some embodiments, the emulsion of this invention is administered by instillation using a syringe with or without an attached needle.

In some embodiments, the emulsion of this invention is administered to block a nerve by administered into a tissue near the nerve that is transmitting the pain signal from the affected pain site, such as surgical incision site or a trauma wound.

In some embodiments, the emulsion of this invention is administered to nerves for both field blocks and peripheral nerve blocks including, but not limited to, TAP blocks, PEC blocks, paravertebral blocks, para-spinal blocks, brachial plexus blocks, cervical plexus blocks, celiac plexus blocks, facet joint blocks, or specific peripheral nerve blocks (for example: trigeminal, ophthalmic, maxillary, interscalene, infraclavicular, axillary, ilioinguinal, penile, femoral, sciatic, popliteal, or saphenous).

In some embodiments, the emulsion of this invention is administered for nerve blocking at a volume up to 1, 2, 3, 4, 5, 6, 7, 8, 9, 10, 11, 12, 13, 14, 15, 16, 17, 18, 19, 20, 25, 30, 40 and 50 mL.

In some embodiments, the emulsion of this invention is administered for nerve blocking at a LA concentration between 0.1% and 3%, preferably between 0.2% and 2%, and most preferably between 0.4% and 2%.

In some embodiments, the emulsion of this invention is administered for nerve blocking after being diluted in a sodium chloride solution, dextrose solution, water or a liquid that is safe for use for nerve block.

In preferred embodiments, the emulsion of this invention is administered for nerve blocking after being diluted in the Normal Saline to an LA concentration between 0.1% and 2%, preferably between 0.2% and 2%, and most preferably between 0.4 and 2%. The reason for preferred range is to achieve a preferred viscosity, injectability, and extended-release profile for the emulsion after the dilution. Too low dilution results in a higher viscosity and difficulty to inject, too high dilution results in a decreased and compromised extended-release profile (EX 11, 12, 13).

In some embodiments, the emulsion of this invention is administered for nerve blocking after being diluted in a sodium chloride solution, dextrose solution, or a liquid that is safe for use for nerve block to a viscosity no more than about 40K, preferably 400 and most preferably 4 centipoise (EX 11, 12).

In some embodiments, the emulsion of this invention is administered into a soft tissue where it provides a higher concentration of LA in the soft tissue than in the blood.

In some embodiments, the emulsion of this invention is administered into a soft tissue wherein LA concentration in the soft tissue is more than 1, 2, 3, 5 and 10 fold of that in the blood.

In some embodiments, the emulsion of this invention is administered into a soft tissue to provide an extended release of LA with the LA plasma concentration exceeding 5 ng/mL after 1, 2, 3, 4, 5, 6 or 7 days (EX 1).

In some embodiments, the emulsion of this invention is administered into a soft tissue to provide a peak-less or low-$C_{max}$ pharmacokinetic profile or a plasma concentration profile with a greatly reduced $C_{max}$ compared to the same dose of the LA in a solution formulation (EX 1).

In some embodiments, the emulsion of this invention is administered into a soft tissue to provide a plasma concentration profile with $C_{max}$ below the cardiotoxic or CNS toxic concentration of the LA, i.e., 3300 ng/mL (EX 1).

In some embodiments, the emulsion of this invention is administered into a soft tissue at a dose of 2-800 mg ropivacaine to provide a $C_{max}$ no greater than 3300ng/mL (EX 1). The $C_{max}$ upper limit is preferred because a higher $C_{max}$ will likely cause cardiovascular or CNS toxicity.

In some embodiments, the emulsion of this invention is administered into a soft tissue at a dose of 2 -800 mg ropivacaine to provide a $T_{max}$ between 0.5 and 48 hr (EX 1).

In some embodiments, the emulsion of this invention is administered into a soft tissue of a human subject at a dose of 2 -800 mg ropivacaine to provide an AUC between 200 and 251,000 ng/mL*hr (EX 1). The range of AUC is preferred because a lower AUC produce a low therapeutic effect, and a higher AUC results in toxicity.

In some embodiments, the emulsion of this invention does not affect the wound healing process of the soft tissue after it is administered into the soft tissue (EX 2, 5).

In some embodiments, the emulsion of this invention does not affect the physical integrity of a suture (EX 6).

In some embodiments, the emulsion of this invention does not affect the physical integrity of a surgical mesh (EX 6).

In some embodiments, the emulsion of this invention provides pain relief for at least about 24 hours.

In some embodiments, the emulsion of this invention provides pain relief between 24 and 48 hours.

In some embodiments, the emulsion of this invention provides pain relief for at least 48 hours.

In some embodiments, the emulsion of this invention provides pain relief between 48 and 72 hours.

In some embodiments, the emulsion of this invention provides pain relief for at least 72 hours.

In the preferred embodiment, the emulsion of this invention is to provide a prolonged pain relief or nerve block.

In the preferred embodiment, the emulsion of this invention is for post-surgical pain management.

In another embodiment, the emulsion of this invention is used for peri-operative nerve block, including but not limited to pre-operative, intra-operative, and post-operative nerve block, to achieve extended pain suppression before, during and after surgeries.

These and other aspects, objects and embodiments will become more apparent when read with the detailed description and drawings that follow.

DETAILED DESCRIPTION

I. Definitions

Figure 1:
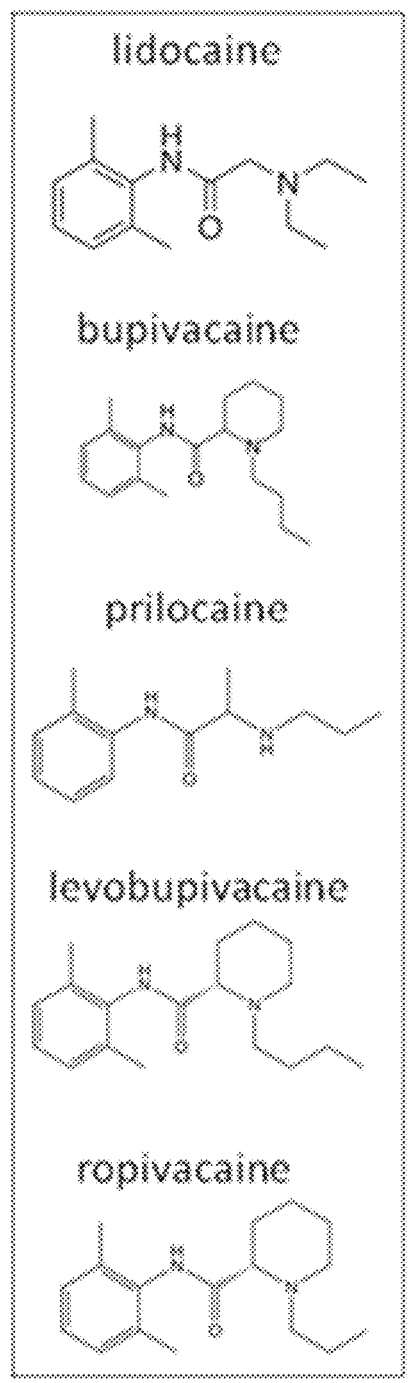
FIG. 1 illustrates schematic structures of amide local anesthetics.

As used herein, the various terms shall have the following definitions.

As used herein, "about" describes a quantity with a range covering 10% expansion from both sides of the target value. For example, "about 100" means any value between 90 and 110 including 90 and 110.

An "antioxidant" is a pharmaceutical additive that can be added to a composition to prevent oxidation of the active drug or an inactive component. Antioxidants include reducing agents, metal ion chelating agents and inert gases. The preferred antioxidants for the emulsions of the present invention are EDTA sodium, cysteine, $CO_2$ gas, ascorbyl palmitate, ascorbic acid, methionine and glutathione.

The term "aqueous phase" refers to a water solution that suspends the oil droplets in an emulsion. In an emulsion of the current invention, the aqueous phase can be separated from the oil phase by an ultrafiltration process, which allows for the separate quantitation of the components in the aqueous and oil phases. In addition to water, the aqueous phase may contain other water-soluble or hydrophilic ingredients. The aqueous phase of the emulsion of the present invention may contain the pH buffer, preservative, antioxidant, metal ion chelating agent or chelator and the small portion of the active drug (LA). In one embodiment, the aqueous phase is a biological fluid such as blood and a body fluid. In one embodiment, the aqueous phase of the present emulsion comprises a reducing agent, a chelator and no more than 10% wt of the LA added. In one embodiment, the aqueous phase of the present emulsion is at a concentration between 0.1% and 90%, preferably between 0.2% and 80%, more preferably between 0.2% and 70%, and most preferably between 0.2% and 66% by weight of the emulsion.

As used herein, "chemical stability" or "chemically stable" means the state of a drug formulation capable of maintaining its active ingredient at no less than 90% of its initial quantity and certain impurity below an acceptable limit. For the emulsion of the present invention is deemed chemically stable if it is capable of maintaining no less than 90% of its initial LA quantity and the LA N-oxide at no more than 0.2% by weight of LA. In one embodiment, an emulsion of this invention is chemically stable. In a preferred embodiment, an emulsion of present invention which maintains LA at no less than 90% of its initial quantity and the LA N-oxide at no more than 0.2% by weight of LA after storing at 25° C. for 1.5 year or preferably 2 years.

As used herein, an "emulsion" is a mixture of immiscible oil phase and aqueous phase. An emulsion can be of oil-in-water or water-in-oil type, is usually optically opaque and possesses a finite physical stability. In certain instances, the composition of this invention is an oil-in-water emulsion, optically semi-transparent or translucent and physically stable. In one embodiment, an emulsion of this invention is the oil-in-water type where the oil phase is made up with discrete oil droplets suspended in a continuous aqueous phase. In another embodiment, an emulsion of present invention is the oil-in-water type after dilution with water or a biological fluid of interest (e.g., body fluid or blood). In another embodiment, an emulsion of this invention is optically semi-transparent or translucent and physically stable. In one embodiment, an emulsion of this invention is an oil-in-water emulsion. In another embodiment, an emulsion of this invention is an oil-in-water emulsion after being mixed with water. In certain other embodiments, removing excess water from an oil-in-water emulsion will generate a water-in-oil emulsion.

As used herein, the term "oil droplet" refers to the emulsion oil phase of the present invention that exists as discrete particles surrounded by the aqueous phase. The oil droplet is made of the water-insoluble components in the emulsion including lecithin and oil. The oil droplets are not liposome particles because they have no lipid bilayer which is a defining liposome structure. The oil droplets are also different from the micelles or micellar particles. Micelles exist in a surfactant solution in water and are of much smaller in size (<100 nm, as compared to the oil droplets of the present invention 200-2500 nm). The surfactants that can form micelles are the water-soluble surfactants such as polysorbate, cremophor, etc. are undesirable due to their toxicity and are excluded in the emulsions of the current invention. Due to the high level of oil (30-70% by weight of the oil phase) present, the oil droplets also differ from the solid lipid nanoparticles or SLN which generally have much less oil than that used in the present emulsion. Physically, the oil droplets are liquid, soft, flexible and easily filterable through a membrane with small pores (0.2-0.45-micron) or injectable through a fine needle whereas liposomes and SLN are solid, inflexible and stiff particles and hard to push through a fine needle or filter.

As used herein, the term "pain relief" means using drugs or other methods to prevent, reduce or get rid of pain; the act of preventing, reducing or getting rid of pain.

As used herein, "particle size" refers to the diameter of the particles or oil droplets in an emulsion of the present invention or after it is diluted in water or a biological fluid. The oil droplet size can have profound impact on the LA's in vitro release, pharmacokinetic profile and injectability of the emulsion of this invention. Very small emulsion droplets (<100 nm) as taught in U.S. Pat. No. 9,517,202 are more difficult to prepare, less stable and tend to release LA rapidly and produce a short pharmacokinetic profile or a short duration of action. On the other hand, large emulsion droplets (>2500 nm) can result in a very viscous emulsion that is hard to expel through a needle, or is not injectable. In certain embodiments, the oil phase in the emulsions of present invention exists in particle size greater than 100 nm. In another embodiments, the particle size in the emulsions of present invention is between 200 nm and 2500 nm, preferably between 200 nm and 500 nm and most preferably between 300 nm and 400 nm.

As used herein, the term of "drug incorporation capacity" defines the maximum amount of a drug that can be loaded in a formulation while still maintaining all desired properties for the formulation. In the emulsion of the present emulsion, the drug incorporation capacity for an LA is about 4% by weight of the emulsion. If an LA is added to exceed 4%, the emulsion will turn cloudy, form a precipitate and/or lose the desired in vitro release profile. In one embodiment, an emulsion of this invention contains no more than 4% wt LA, preferable no more than 3.5% wt LA, and most preferably at 0.5%, 1%, 1.5%, 2%, 2.5% or 3% wt LA.

As used herein, "filterable" means the ability of the emulsion of the present invention to pass through a filter membrane of a certain pore size such as 0.2-5-microns without a significant (>10%) loss of LA adsorbed onto the membrane. In one embodiment, an emulsion of this invention is filterable through a filter with pore size in between 0.2 and 5 micron. In another embodiment, an emulsion of this invention is filterable through a filter with a pore size of 5 micron, 1.2-micron, 0.8-micron, 0.45-micron or 0.2-micron. In one embodiment, an emulsion of this invention is filterable without any organic solvent. In a preferred embodiment, an emulsion of this invention is filterable with either an organic solvent, aqueous phase or a mixture thereof.

As used herein, the term "fine needle" or "needle" includes a small-bore, hollow hypodermic needle which is attached to a syringe or catheter for injection and infiltration. The outer diameter of the needle is indicated by the needle gauge system. According to the Stubs Needle Gauge system, hypodermic needles in common medical use range from 7 (the largest) to 33 gauge (G) (the smallest). In one embodiment, an emulsion of this invention is extrudable or injectable through a needle or catheter using a syringe. In a preferred embodiment, an emulsion of this invention is extrudable through a needle ranging from 18 to 27G, preferably 18G to 25G and most preferably 18G to 22G using a syringe of size ranging from 1 mL to 50 mL, preferable 10 mL. In another preferred embodiment, an emulsion of this invention is extrudable through a catheter (6"-24" long) attached to a needle (16-25G) using a syringe of size ranging from 1 mL to 50 mL. This needle-catheter-syringe combination is particularly useful for nerve block using the LA emulsion of the present invention.

As used herein, the term "hydrophobicity" or being "hydrophobic" means that an LA molecule of interest has a log P of 1.5 or greater, wherein P is an octanol/water partition coefficient. A free base or unionized form of an LA is generally insoluble in water and has a high log P or is hydrophobic. In contrast, an ionized or a salt form of the same LA is generally soluble in water, has a log P below 1.5 or is non-hydrophobic. For example, ropivacaine as a free base has a log P of 2.9 (P=octanol:water partition coefficient=794) and is insoluble in water, whereas ropivacaine hydrochloride salt is non-hydrophobic and has a log P of 1.1

(P=14). In one embodiment, an emulsion of this invention is able to incorporate an LA in either its free base or salt form, i.e., regardless of the LA hydrophobicity. In another embodiment, an emulsion of this invention provides a similar pharmacological activity for an LA free base or it salt (Ex 3).

As used herein, the term "infiltration" means the injection into a tissue at one or multiple sites. For example, LA can be injected at more than one point into the surgical wound tissue so as to infiltrate an area to provide analgesic effect or pain relief for the entire area.

As used herein, the term "injectable" means when 10 mL of a liquid can be expelled through a fine needle with a 10 mL syringe at 25 Newton force in less than 10 min (Ex 8).

As used herein, the term "instillation" means the direct or topical administration or application (not injection) of drug product onto a tissue. For example, LA can be topically administered to the surgical wound as instillation to provide analgesic effect or pain relief for the entire wound.

As used herein, the term "in vitro release" refers to the rate and extent of dissociation of LA from the formulation (e.g., emulsion of this invention) to become an unbound or free in water or an aqueous solution of interest (e.g., saline or a biological fluid) as studied in a test tube or vessel. In vitro release studies thus reveal the onset, rate and duration of LA release by the emulsion. Under a set of in vitro release test conditions, the onset is quantified by the time to reach 20% of the maximum LA concentration, the rate by the time to reach 50% of the maximum LA concentration and the duration the time to reach the maximum LA concentration. If two LA formulations don't share the same in vitro release profile, they are not considered equivalent in their biological activities, i.e., not bioequivalent. Differences in the in vitro release profile also indicate that the two formulations are structurally different even though they may be made with the same or similar materials (Ex 7). Furthermore, the process conditions for making the emulsion of the present invention can have profound impact on the in vitro release. The type and quantity of LA added, the materials used in the aqueous and oil phase phases, their net and relative (ratio) quality, the order of their addition, the droplet size and, optionally, ingredients such as an organic solvent in the emulsion of the present invention all can alter the in vitro release profile. Therefore, in one embodiment, the emulsion of the present invention provides an in vitro release profile that is slower and longer than a solution of the same LA and that is different from a liposome-based LA formulation (Ex 7).

As used herein, a "local anesthetic" refers to an amide local anesthetic drug molecule having one of the chemical structures as shown in FIG. 1.

As used herein, "LA-oil droplet binding" means the non-covalent binding between LA and oil droplets in the emulsion of the present invention. The non-covalent binding is measured by separating the unbound or free LA molecules from the LA bound to oil droplets in water or aqueous medium of interest, e.g., blood or a biological fluid and then determining their respective concentrations. The separation of the free from the bound LA can be obtained by ultrafiltration and the LA concentration can be measured by HPLC. The extent of LA-oil droplet binding ratio is expressed in a concentration ratio (LA-oil droplet binding (%)=Conc of Bound LA/Conc of Total LA×100). In one embodiment, an emulsion of this invention has an LA-oil droplet binding LA-oil droplet binding (%) of no less than 90% for an LA. In a preferred embodiment, an emulsion of this invention has an LA-oil droplet binding LA-oil droplet binding (%) of no less than 90% for an LA regardless its hydrophobicity or log P (i.e., greater or less than 1.5).

As used herein, "lecithin" is a mixture of phospholipids derived from a natural source. Injectable lecithin includes lecithin derived from egg or soybean, which have been purified and are substantially free from irritating, allergenic, inflammatory agents or agents that cause other deleterious biological reactions. For this invention, the preferred lecithins include those that contain more than 75% w/w phosphotidylcholine (PC), are insoluble in water and essentially free of lysolecithin (i.e., containing no more than 1-4% lysolechithin by weight). A high PC content makes the lecithin relatively soft and produces relatively smoother and more injectable emulsion. Lysolecithin is hemolytic and undesirable for the safety reasons. Examples of the preferred lecithins include, but are not limited to, lecithin products by the trade names of LIPOID S 75, LIPOID S 100, LIPOID E 80, and Phospholipon 90 G. Some fatty acid chains on the lecithin molecule are unsaturated and can undergo oxidation to form peroxides which can in turn oxidize the LA to form the N-oxide of LA. Therefore, in one embodiment, the emulsion of this invention contains an antioxidant and/or a metal ion chelator or a combination thereof to inhibit the lecithin oxidation. Some lecithins are hydrogenated to contain only the saturated fatty acids. While these hydrogenated lecithins are less sensitive to oxidation, they have a higher melting point and produce emulsions that are hard (cream like) and difficult to inject. In the present emulsion, lecithin is needed to form the oil droplets, bind the LA and provide a slow release of LA. If lecithin is used at below 20% wt of the emulsion, the emulsion losses its ability to provide a slow release or the prolonged action profile for LA. On other hand, if the lecithin is over 70% wt of the emulsion, the emulsion becomes hard and is difficult to inject. Thus, the preferred amount of lecithin used in the present emulsion is between 20% and 70% wt of the emulsion weight. In one embodiment, the preferred lecithin for the emulsion of this invention has a PC content no less than 75% wt. In another embodiment, the preferred lecithin for the emulsion of this invention has no more than 1-4% wt lysolecithin. In another embodiment, the preferred lecithin is derived from soybean or egg yolk. In another embodiment, the preferred lecithin is selected from the group consisting of LIPOID S 75, LIPOID S 100, LIPOID E 80, and Phospholipon 90 G or a mixture thereof In another embodiment, the lecithin used in the present emulsion contains no more than 25% wt of lecithin with completely saturated fatty acid side chains or hydrogenated lecithin. In one embodiment, the amount of lecithin used in the present emulsion is between 20% and 70%, preferably between 40% and 60% and most preferably between 50% and 60% of the emulsion by weight (w/w).

As used herein, "lipid bilayer" refers to the characteristic structural membrane surrounding a liposome particle or vesicle. A liposome is a spherical-shaped vesicle that is composed of one or more phospholipid bilayers, which closely resemble the bilayer structure of cell membranes. The ability of liposomes to encapsulate hydrophilic or lipophilic drugs has allowed these vesicles to become useful drug delivery systems (e.g., Exparel®). Other lipid-based particles or vesicles used on drug formulation such as emulsions, micelles, and solid lipid nanoparticles (SLN) are free of the lipid bilayer (See, Solid Lipid Nanoparticles, https://em.wikipedia.org/wiki/solid_lipid_nanpartice).

Figure 4:
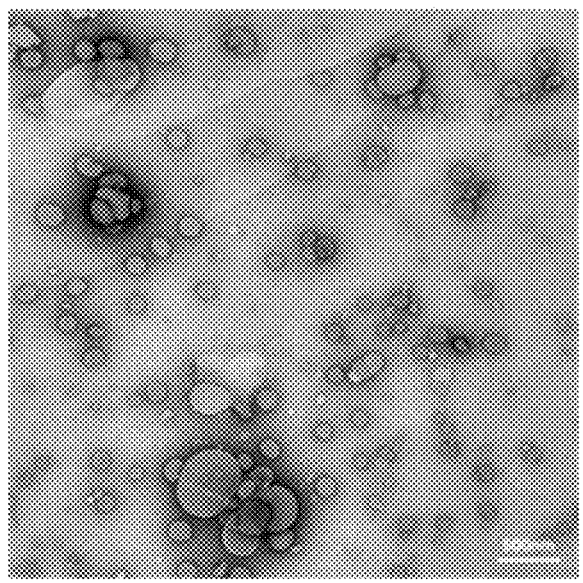
FIG. 4 illustrates electron micrographs showing TEM images of particles or droplets in the emulsion of the present invention undiluted emulsion (upper panel) and diluted emulsion (lower panel) and the typical liposomal particles of a well-characterized and FDA-approved liposomal drug (Ambisome™). An emulsion droplet has a solid core (i.e., without the empty internal void) and the particle has no distinctive membrane, whereas a liposome vesicle has an empty core and surrounded by the distinctive bilayer lipid membrane.
Figure 4:
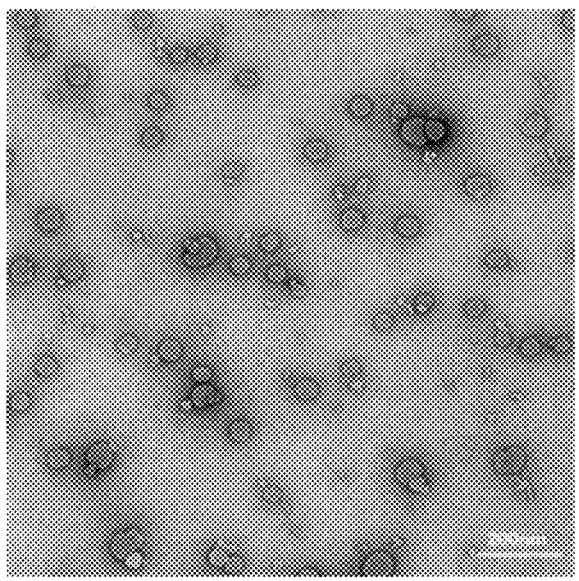
Figure 4:
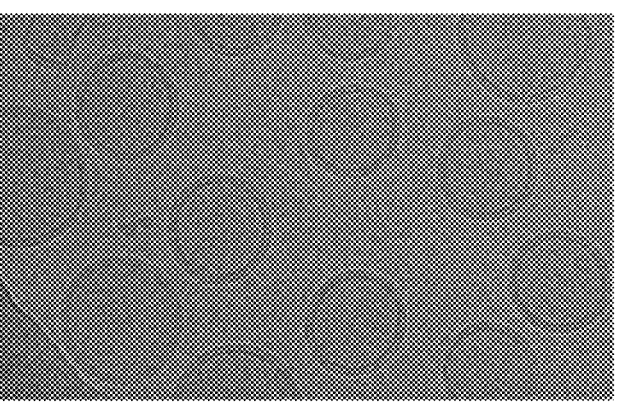

Although these lipid-based formulations may share the same raw materials such as phospholipids, oil and water, they differ significantly from each in not only their structure, but also their drug delivery properties such as in vitro release, drug incorporation capacity, stability, and pharmacokinetics. Liposome and emulsion LA formulations are therefore not considered bioequivalent and are not interchangeable in their use. The presence of the lipid bilayer can be determined by electron microscope visualization, thus revealing the structural differentiation between a liposome and a non-liposome particle. FIG. 4 exhibits an electron micrograph (EM) image of known liposome drug formulation (Ambisome®) with its lipid bilayer clearly visible and an EM image of an emulsion droplet of the present invention where the lipid bilayer is clearly not present.

Figure 3:
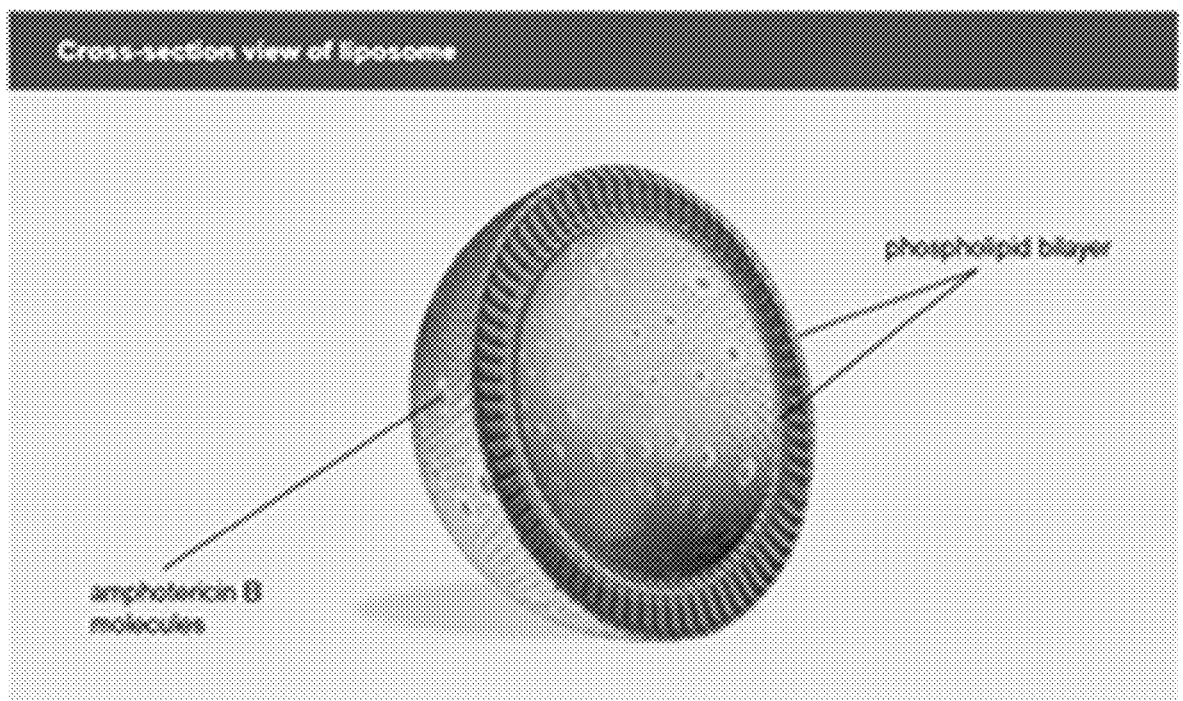
FIG. 3 illustrates a schematic presentation of the liposomal bilayer membrane

As used herein, "liposome" refers to a spherical-shaped vesicle that is composed of one or more phospholipid bilayers (FIG. 3), which closely resembles the structure of cell membranes. The ability of liposomes to encapsulate hydrophilic or lipophilic drugs and be injectable have allowed these vesicles to become useful drug delivery systems.

The term "metal ion chelating agent or chelator" includes a metal ion chelator that is safe to use in an injectable product. A metal ion chelator works by binding to a metal ion and thereby reduces the catalytic effect of that metal ion on the oxidation, hydrolysis or other degradation reactions. Metal chelators that are useful in this invention may include ethylenediaminetetraacetic acid (EDTA, edetate), glycine and citric acid and the respective salts or a mixture thereof. In one embodiment, the emulsion of this invention contains an antioxidant and/or a metal ion chelator or the combination thereof.

As used herein, the term "nerve block" means a procedure in which an anesthetic or analgesic agent was injected into the area surrounding or directly near a nerve to block the pain, sensation, or movement of certain portion of the body. A nerve block can be a regional or peripheral nerve block and is a form of regional anesthesia or pain relief.

Figure 2:
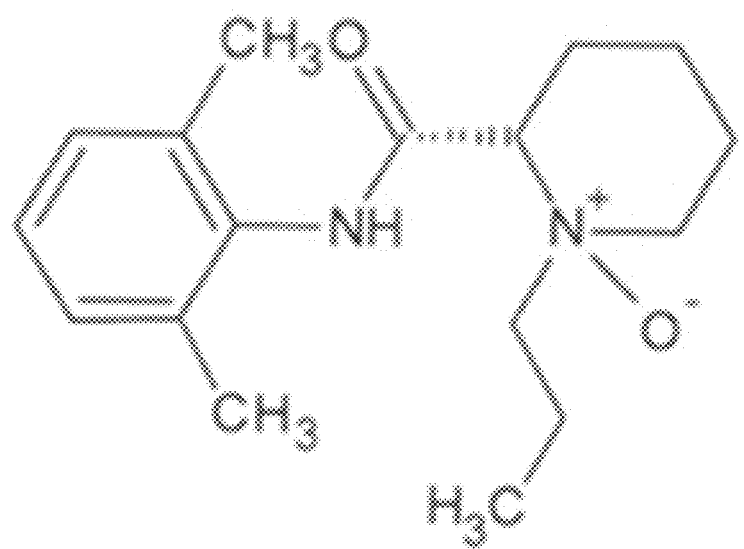
FIG. 2 illustrates the structure of ropivacaine N-oxide

As used herein, "N-oxide" refers to the oxidation product of an LA where an oxygen is attached covalently to the nitrogen atom (N) on the LA structure. For example, ropivacaine N-oxide is depicted in FIG. 2. The oxidation of the nitrogen atom is the major degradation product of an LA in a formulation containing lecithin or oil and therefore must be kept to below 0.2% (based on the weight of the LA). The 0.2% limit is the Identification and Qualification Thresholds for an impurity according to FDA's Guidance for Industry Q3B(R2) Impurities in New Drug Products. In one embodiment, the emulsion of this invention contains an antioxidant and/or a metal ion chelator or a combination thereof to inhibit the formation of N-oxide. In a preferred embodiment, the emulsion of this invention contains no more than 0.2% (by wt of LA) N-oxide.

As used herein, "neutral pH" is in the range of 4 to 8, preferably 5.2 to 7.2.

As used herein, an "oil-in-water emulsion" is an emulsion wherein the oil phase is in the form of small droplets (the dispersed phase) that are suspended or dispersed in the aqueous phase (the continuous phase) and "water-in-oil emulsion" refers to a form where small water droplets suspended or dispersed in the oil phase. In a preferred embodiment, the emulsion of this invention is an oil-in-water emulsion. In another preferred embodiment, the emulsion of this invention is a water-in-oil emulsion that converts to an oil-in-water emulsion after it is diluted in water or a biological fluid such as blood. In another embodiment, the emulsion of this invention is a mixture of oil-in-water and water-in-oil emulsions.

As used herein, "oil phase" refers to the water-immiscible phase of an emulsion (o/w) comprising oil and phospholipid. The oil phase may also contain other lipophilic additives, including antioxidants and antimicrobial preservatives, etc. and LA as in the emulsions of present invention. In one embodiment, the emulsion of present invention contains an oil phase at a concentration between about 20% and 99.5% of the emulsion weight. When the oil phase is below 20% wt, the emulsion loses its ability to provide the desired extended release and prolonged action of an LA. On the other hand, oil phase can be as high as 99.8%, preferable 99.7% and more preferable 99.5% of the emulsion weight. An emulsion with oil phase greater than 99.8% can be difficult to prepare since the residual water (<0.2%) is difficult to remove using the current emulsion preparation procedure for the emulsion of the present invention (Ex 18). The emulsion is primarily of oil-in-water type when the water content exceeds about 50% of the emulsion weight or primarily water-in-oil type when the water content is less than about 5% of the emulsion weight. When the water content is between about 5% and about 50% of the emulsion weight, the emulsion comprises both oil-in-water and water-in-oil types. The water-in-oil emulsion may convert completely or partially to the oil-in-water type when it is injected or instilled into the human body or diluted with a biological fluid such as blood.

As used herein, the term "organic solvent" refers to the water-immiscible solvents that are safe to inject into human. Example of organic solvents include, but not limited to, glycerin, ethanol, alcohol, benzyl alcohol, propylene glycol, polyethylene glycol, or a combination thereof. The main purpose of adding an organic solvent to an emulsion of the present invention is to reduce the viscosity of the emulsion. An organic solvent can also serve as an antimicrobial preservative to allow the emulsion to be used for a prolonged period of time. The amount of the organic solvent has to be, however, controlled within a range of about 2% to 12% by weight of the emulsion. If the organic solvent added to below 4%, the viscosity-reducing effect may not be achieved, but the organic solvent exceeds 12% of the emulsion weight, the oil-in-water emulsion of this invention will be destroyed with greatly increased oil droplets size (e.g., >1-5 micron, due to droplets aggregation) and the emulsion would turn into a thick paste, rendering it difficult to inject. In one embodiment, an emulsion of present invention contains 0% organic solvent. In another embodiments, an emulsion of present invention contains an organic solvent at 2% to 12% by weight of the emulsion, preferable 4% to 10% by weight of the emulsion, or more preferably 6% to 8% by weight of the emulsion.

As used herein, the term "pain intensity scale" or "pain intensity score", or "pain scale" or "pain score" is a tool to help assess a person's pain level. A person usually self-reports their pain using a specially designed scale, sometime with the help of a doctor, parent, or guardian. Commonly used pain scale include but not limited to numerical rating scale (NRS), Visual analog scale (VAS), Categorical scales, Wong-Baker Faces Pain scale; "pain score at rest or NRS-R and with activities (NRS-A)" means a numerical rating scale (NRS) for pain relief that requires the patient to rate their pain on a defined scale. For example, 0-10 where 0 is no pain and 10 is the worst pain imaginable. Commonly used NRS are 11 point (0-10), 21 point (0-20) and 101 point (0-100). The NRS-R is the pain score reported when the subject is at rest. The NRS-A is the pain score reported when or after the subject performed certain activities or movements.

As used herein, the term "pH buffering agent" or "pH buffer salt" includes ionizable pH buffer salts such as phosphate, acetate, citrate, bicarbonate, and the like, with a counter-ion such as ammonium, sodium or potassium etc.

In a preferred aspect, the emulsion of the present invention is at a pH between about 4 and about 8, more preferably, between about pH 4 to about 7, such as at about 4.0, 4.2, 4.4, 4.6, 4.8, 5.0, 5.2, 5.4, 5.6, 5.8, 6.0, 6.2, 6.4, 6.6, 6.8, 7.0 or 7.2. The pH of the emulsion is achieved by the combining all components according to the emulsion composition of this invention, adding an acid (e.g., HCl, acetic acid, phosphoric acid) and/or base (e.g., NaOH, KOH, arginine, lysine) to adjust to the target pH. When the pH is lower than pH 4, the emulsion is irritating and may cause injection site reaction. When pH is higher than 7, the LA degradation is accelerated and the emulsion forms precipitates readily.

As used herein, "pharmacologically active" or "pharmacological activity" of an LA refers to the in vivo or in vitro measurement of the intended biological activity of an LA. The pharmacological activity of LA formulated in an emulsion of the present invention is not compromised as compared to the free or unbound LA (Ex. 2). This is in stark contrast to the general knowledge that emulsions decrease LA's biological activity, indicating that the emulsions of the current invention are functionally different from other emulsions, such as Intralipid, that are commonly used to deactivate or as antidotes for LA. In one embodiment, an emulsion of present invention maintains its LA pharmacological activity within the 50% to 150% range of the free LA activity at the same dose.

As used herein, the term of "pharmacokinetic profile" or PK profile" refers to the blood concentration profile over time of a drug following its administration to an animal or human subject. For the present emulsion, the PK profile is expressed in LA plasma concentration over time with the following four key parameters.

$C_{max}$: The maximum plasma LA concentration $T_{max}$: Time to reach $C_{max}$ AUC: Area under the curve which measures the bioavailability of the LA $T_{1/2}$: Elimination half-life In one embodiment, an emulsion of present invention exhibits PK parameters as listed in Ex 1. In another embodiment, an emulsion of present invention exhibits a human PK profile with a $C_{max}$ at between 224 and 1280 ug/mL, $T_{max}$ at between 2.18 and 30.1 hours, $AUC_{0-inf}$ at between 10,200 and 35,100 ng*h/mL, and a $T_{1/2}$ at between 16.3 and 33.7 hours, following injection and infiltration into a surgical incision of a 2% wt ropivacaine emulsion of the present invention in human at 200 mg dose.

As used herein, "phospholipid" refers to any triesters of glycerol having two fatty acids and one phosphate ion which is covalently attached to a small organic molecule (such as choline, ethanolamine, glycerol, serine or nothing. Exemplary phospholipids hence include phosphatidylcholine (PC), phosphatidylethanolamine (PE), phosphatidylglycerol (PG), phosphatidylserine (PS), and phosphatidic acid (PA). The fatty acids generally have from about 10 to about 18 carbon atoms with varying degrees of saturation. These phospholipids can be obtained from natural sources or made synthetically. The naturally derived phospholipids are referred to as lecithin. Examples of synthetic phospholipids are 1,2-dimyristoyl-sn-glycero-3-phosphocholine (DMPC), 1,2-distearoyl-sn-glycero-3-phosphoethanolamine (DSPE), 1,2-dimyristoyl-sn-glycero-3-phosphoglycerol, sodium salt (DMPG, Na) and 1,2-dipalmitoyl- sn-glycero-3-phospho-L-serine, sodium salt (DPPS, Na). A synthetically produced phospholipid is generally difficult to incorporate into the oil phase, has limited safety and is expensive. In certain embodiments, the emulsions of the current invention are substantially free of a synthetic phospholipid. In another embodiment, lecithin is the preferred phospholipids for the emulsion of this invention.

As used herein, "physical stability" or "physically stable" is in reference to an emulsion of this invention is capable to maintaining certain desired physical properties such as visual uniformity, absence of LA precipitation, viscosity and in vitro release profile after 2 years at 25° C. In certain embodiments, the emulsions of the current invention remain visually uniform, substantially free any LA precipitates and the same viscosity (between about 90% and about 110% of the initial value) after about 2 years at 25° C. In another embodiment, the emulsions of the current invention retain the same in vitro release profile by maintaining the onset, rate and duration all with about 50% to about 150% of their initial values.

As used herein, "reducing agents" useful in this invention include, but are not limited to, ascorbic acid, ascorbate, ascorbyl palmitate, metabisulfite, propyl gallate, butylated hydroxyanisole, butylated hydroxytoluene, tocopherol, cysteine, methionine, citric acid, citrate, a reducing sugar such as glucose, fructose, glyceraldehyde, galactose, lactose, maltose, a salt or a mixture thereof. In certain embodiment, the emulsion of the current invention contains a reducing agent. In a preferred embodiment, the emulsion of the current invention contains a reducing agent selected from the group consisting of ascorbic acid, ascorbyl palmitate, tocopherol, cysteine, methionine. In another embodiment, the reducing agent used is between 0.1% and 3% of the emulsion weight.

As used herein, the term of "semi-transparent" or "translucent" refers to the partial transparency or clarity of a liquid. A semi-transparent or translucent liquid drug allow visual examination of foreign particles and microbial contamination in the liquid. Therefore, being semi-transparent or translucent is much preferred over being opaque (like milk). The degree of transparency of a liquid can be quantitated by measuring by the light transmission (T, %) using a UV-vis spectrophotometer at a fixed wavelength (e.g., 700 nm). An emulsion of the present invention typically has a T value of no less than 50% at 700 nm using a 10 mm path length quartz cuvette. Under the same conditions, water has a T value about 100% and ordinary cow's milk has a T value of less than 10%. In one embodiment, an emulsion of this invention is semi-transparent or translucent. In another embodiment, an emulsion of present invention has a T value (measured at 700 nm using a 10 mm path length quartz cuvette) of more than 25%, preferably more than 40%, and more preferably 50%.

As used herein, the term "soft tissue" means is all the tissue in the body that is not hardened by the processes of ossification or calcification such as bones and teeth. Soft tissue connects, surrounds or supports internal organs and bones, and include, but not limit to, muscle, tendons, ligaments, fat, fibrous tissue, lymph and blood vessels, fasciae, synovial membranes, or skin.

As used herein, the term "substantially free" means less than 1% of the total composition weight.

As used herein, "solution" refers to a clear, homogeneous mixture composed of only one phase. The emulsion of present invention is not a solution because it has oil droplets (one phase) suspended in an aqueous phase (a second phase).

As used herein, "surfactants" refers to water-soluble compounds that lower the surface tension of a liquid or the interfacial tension between oil and water. Examples of surfactants are polysorbates, spans, cremophor, vitamin E TPGS, sodium lauryl sulfate, poloxamer, and Tyloxapol, etc. The emulsion of the current invention is substantially free of a surfactant, preferably is substantially free of the ionizable cationic lipid, a PEGylated lipid, or cholesterol that are commonly used in solid lipid nanoparticles (SLN).

As used herein, the term "surgical mesh" means a type of netting sheet of plastic, organic, or biological material that may be implanted to support various tissues or organs during surgery. Surgical mesh can be made from inorganic, organic, polymer and biological materials.

As used herein, the term "suture" means a medical device used to hold body tissues together after an injury or surgery. Application generally involves using a needle with an attached length of thread.

As used herein, "ultrafiltration" (UF) refers to a variety of membrane filtration techniques in which hydrostatic pressure forces a liquid against a semipermeable membrane. Suspended solids, oil droplets or solutes of high molecular weight or size are retained, while water and low molecular weight solutes, e.g., free drug, pass through the membrane. Ultrafiltration (e.g., with a 30K Dalton MW cutoff membrane) is used to separate the oil phase (oil droplets get retained on the membrane) and the aqueous phase (passes through the membrane) of the present emulsion. The separated oil and aqueous can then be analyzed for LA concentration in each phase.

As used herein, "vegetable oil" refers to oil derived from plant seeds or nuts. Exemplary vegetable oils include, but are not limited to, almond oil, borage oil, black currant seed oil, corn oil, safflower oil, soybean oil, sesame oil, cottonseed oil, peanut oil, olive oil, rapeseed oil, coconut oil, palm oil, canola oil, castor oil etc. Vegetable oils typically contain long-chain triglycerides, that are formed when three fatty acids (usually about 14 to about 22 carbons in length and having chains that with unsaturated bonds in varying numbers and locations, depending on the source of the oil) form ester bonds with the three hydroxyl groups on glycerol. In certain embodiments, vegetable oils of highly purified grade (also called "super refined") are generally used to ensure safety and stability of pharmaceutical-grade oil-in-water emulsions. For the present invention, the preferred oils are soybean oil, corn oil and sesame oil. Compared to other oils, castor oil is more hydrophilic because it has a hydroxy group on the fatty acid side chain. In one embodiment, castor oil is not used because the emulsion physically less stable when castor oil used. Because some fatty acid chains on the oil molecule are unsaturated and can undergo oxidation to form peroxides which can in turn oxidize the LA in the same formulation. Therefore, in one embodiment, the emulsion of this invention contains an antioxidant and/or a metal ion chelator or a combination thereof to inhibit the oil oxidation. In one embodiment, the emulsion of this invention contains about 10% to about 50%, preferably about 20% to about 40% or more preferably about 30% to about 40% vegetable oil by weight of the emulsion. When the oil is at lower than 10%, the emulsion is very hard, difficult to filter and inject, on the other hand, when the oil exceeds 50%, the emulsion formed is white, opaque, creamy and viscous and also difficult to filter and inject. In another embodiment, the lecithin-to-oil weight ratio in the emulsion of this invention is at between 7:1 and 2:5, preferably between 3:1 and 1:1, and more preferably between 2:1 and 5:4.

As used herein, "water-soluble" describes a solid or liquid solute that can dissolve in water to form a homogeneous solution to an extent of no less than one weight part of solute in every ten weight parts of water.

As used herein, "water-soluble surfactants" are compounds help solubilize compounds to form a clear and one-phase aqueous solution by lowering the interfacial surface between water and another liquid or between water and a solid. Water-soluble surfactants include any surfactant or surface-active agent with a Hydrophilic-Lipophilic Balance (HLB) greater than 7. Examples of water-soluble surfactants include, but not limited to, polysorbate, span, lysolecithin, labrasol, cremophor, solutol, gelucire, SDS, and TPGS etc. In contrast, lecithin is NOT a water-soluble surfactant because it is not soluble in water. A water-soluble surfactant is commonly used in emulsions, but is not desirable for the emulsion of this invention because most of them can cause hemolysis (disruption of red blood cell membranes) and irritation or pain at the injection site. In certain embodiments, the emulsion of the present invention is substantially free of a water-soluble surfactant. In a preferred embodiment, the emulsion of the present invention is substantially free of lysolecithin.

As used herein, "wound healing process" or "wound healing" means a living organism's replacement of destroyed or damaged tissue by newly produces tissue. It typically involved four stages: hemostasis, inflammation, proliferation and maturation. A good wound healing process leads to no scar formation and weakened physical strength of the sealed tissue.

II. Embodiments

The present invention provides an emulsion composition, comprising, consisting essentially of, or consisting of:
   a) a local anesthetic,
   b) an oil phase, and
   c) an aqueous phase
wherein
   i. the local anesthetic is at a concentration up to 4% by weight of the emulsion,
   ii. the oil phase is at a concentration between about 20% and 99.8% by weight of the emulsion,
   iii. the oil phase comprises lecithin and vegetable oil at weight ratio between 7:1 and 2:5, and
   iv. the emulsion contains particles or droplets with an average diameter between about 200-2500 nanometers.

The present invention provides an emulsion composition, comprising, consisting essentially of, or consisting of:
   a) Ropivacaine or a salt thereof,
   b) an oil phase, and
   c) an aqueous phase
wherein
   i. the ropivacaine is at a concentration between 0.5% and 4% by weight of the emulsion,
   ii. the oil phase is at a concentration between about 20% and 99.8% by weight of the emulsion,
   iii. the oil phase comprises lecithin and vegetable oil at weight ratio between 2:1 and 5:4, and
   iv. the emulsion contains particles or droplets with an average diameter between about 200-2500 nanometers.
   v. the emulsion comprises a reducing agent and a metal ion chelator, and
   vi. the pH of the emulsion is between 4 and 7.

The present invention provides an emulsion composition, comprising, consisting essentially of, or consisting of:
   a) Ropivacaine hydrochloride,
   b) an oil phase consists of soy lecithin and sesame oil, and
   c) an aqueous phase consists of EDTA sodium, cysteine and water wherein i. the ropivacaine is at a concentration between 0.5% and 4% by weight of the emulsion,
ii. the soy lecithin and vegetable oil are at a weight ratio between 2:1 and 5:4,
iii. the emulsion contains particles or droplets with an average diameter between about 200-2500 nanometers.
iv. the oil droplets have a concentration of about between 33% and 99.5% of the weight of the emulsion, and
v. the pH of the emulsion is between 4 and 7.

III. Methods of Making the Emulsions

In one embodiment, the present invention provides a method for preparing an emulsion composition of the present invention, comprising, consisting essentially of, or consisting of:
Step 1. Combine oil phase components including lecithin and vegetable oil
Step 2. Homogenize to form a smooth semi-solid paste
Step 3. Combine the aqueous phase components including LA, reducing agent, metal chelator and water. Mix to form an aqueous solution
Step 4. Combine the aqueous solution and the paste
Step 5. Homogenize to form an oil-in-water emulsion with oil droplets having a mean diameter between 200 and 2500 nm
Step 6. Adjust emulsion pH to between 4 and 7
Step 7. Adjust the water content by adding more or removing some water by vacuum drying to between 20% and 99.8%, as needed
Step 8. Optionally, add a miscible organic solvent (e.g., ethanol)
Step 9. Filter the emulsion IV. Methods of Use Pain Susceptible to Management with Local Anesthetics Administration of a LA emulsion of this invention can be used to provide pain relief that is associated with any of a wide variety of disorders, conditions, or diseases. Causes of pain may be identifiable or unidentifiable. Where identifiable, the origin of pain may be, for example, of malignant, non-malignant, infectious, non-infectious, or autoimmune origin.

Subjects who are not presently suffering from a disease or condition, but who are susceptible to such may also benefit from prophylactic pain relief method of this invention, e.g., prior to traumatic surgery. Pain amenable to therapy according to the invention may involve prolonged episodes of pain alternating with pain-free intervals, or substantially unremitting pain that varies in severity.

In general, pain can be somatogenic, neurogenic, or psychogenic. Somatogenic pain can be muscular or skeletal (i.e., osteoarthritis, lumbosacral back pain, posttraumatic, myofascial), visceral (i.e., chronic pancreatitis, ulcer, irritable bowel), ischemic (i.e., arteriosclerosis obliterans), or related to the progression of cancer (e.g., malignant or non-malignant). Neurogenic pain can be due to posttraumatic and postoperative neuralgia, can be related to neuropathies (i.e., diabetes, toxicity, etc.), and can be related to nerve entrapment, facial neuralgia, perineal neuralgia, post-amputation, thalamic, causalgia, and reflex sympathetic dystrophy. Each possibility is a separate embodiment of the invention.

Specific examples of conditions, diseases, disorders, and origins of pain amenable to management include, but are not limited to, post-operative pain (also referred to as post-surgical pain), cancer pain (e.g., metastatic or non-metastatic cancer), chronic inflammatory disease pain, neuropathic pain, iatrogenic pain (e.g., pain following invasive procedures or high dose radiation therapy, e.g., involving scar tissue formation resulting in a debilitating compromise of freedom of motion and substantial chronic pain), complex regional pain syndromes, failed-back pain (chronic back pain), soft tissue pain, joints and bone pain, central pain, injury (e.g., debilitating injuries, e.g., paraplegia, quadriplegia, etc., as well as non-debilitating injury (e.g., to back, neck, spine, joints, legs, arms, hands, feet, etc.), arthritic pain (e.g., rheumatoid arthritis, osteoarthritis, arthritic symptoms of unknown etiology, etc.), hereditary disease (e.g., sickle cell anemia), infectious disease and resulting syndromes (e.g., Lyme disease, AIDS, etc.), chronic headaches (e.g., migrans), causalgia, hyperesthesia, sympathetic dystrophy, phantom limb syndrome, denervation, and the like. Pain can be associated with any portion(s) of the body, e.g., the musculoskeletal system, visceral organs, skin, nervous system, etc. Each possibility is a separate embodiment of the invention.

Cancer pain is an example of one broad category of pain that may be alleviated using the emulsions of local anesthetic. One of the underlying causes of cancer pain is the severe local stretching of tissues by the neoplastic lesion. For example, as the cancer cells proliferate in an unrestricted manner, the tissues in the local region of cancer cell proliferation are subjected to mechanical stress required to displace tissue and accommodate the increased volume occupied by the tumor mass. When the tumor burden is confined to a small enclosed compartment, such as the marrow of a bone, the resulting pressure can result in severe pain. Another cause of pain can result from the aggressive therapies used to combat the patient's cancer, e.g., radiation therapy, chemotherapy, etc. Such cancer therapies can involve localized or widespread tissue damage, resulting in pain.

Pain associated with any type of malignant or non-malignant cancer may be amenable to alleviation according to the methods described herein. Specific examples of cancers that can be associated with pain (due to the nature of the cancer itself or therapy to treat the cancer) include, but are not necessarily limited to lung cancer, bladder cancer, melanoma, bone cancer, multiple myeloma, brain cancer, non-Hodgkin's lymphoma, breast cancer, oral cancers, cervical cancer, ovarian cancer, colon cancer, rectal cancer, pancreatic cancer, dysplastic nevi, endocrine cancer, prostate cancer, head and neck cancers, sarcoma, Hodgkin's disease, skin cancer, kidney cancer, stomach cancer, leukemia, testicular cancer, liver cancer, uterine cancer, and aplastic anemia. Certain types of neuropathic pain can also be amenable to treatment according to the invention.

Chronic back pain, which may also be amenable to management using the methods described herein, is another broad category of pain. Chronic back pain is generally due to one or more of the following six causes: (i) stress on intervertebral facet joints, caused by slippage, arthritis, wedging, or scoliosis; (ii) radiculopathy, the mechanical compression of the nerve root due to bulging discs or tumors; (iii) tendonitis or tendon sprain; (iv) muscle spasm or muscle sprain; (v) ischemia, a local insufficiency in circulatory flow; and (vi) neuropathy, damage to nervous tissue of metabolic etiology or arising from cord tumors or central nervous system disease.

The emulsions described herein can be used for a variety of therapeutic purposes that require a long-acting or slow release formulation of LA.

As a common medical practice, emulsions have always been used to deactivate a LA or as an antidote for LA overdose. It is well documented that an emulsion (contains no drug) is commonly used to decrease the cardiovascular effect or toxicity of a LA. Various researchers demonstrated clearly that emulsions can deactivate LAs resulting in loss of LA's pharmacological effect and its toxicity (See, Zausig, York A. et al., Lipid Emulsion Improves Recovery from Bupivacaine-Induced Cardiac Arrest, but Not from Ropivacaine- or Mepivacaine-Induced Cardiac Arrest, Anesthesia & Analgesia: October 2009 - Volume 109 -Issue 4 - p 1323-1326; E. Litonius, et al, Effect of intravenous lipid emulsion on bupivacaine plasma concentration in humans, Anaesthesia 2012, 67, 600-605; Lotte C. G. et al, Systematic review of the effect of intravenous lipid emulsion therapy for local anesthetic toxicity, Clinical Toxicology, 2016, VOL. 54, NO. 3, 167-193, http://dx.doi.org/10.3109/15563650.2015.1121270).

Using an emulsion to deliver a pharmacologically active LA is thus contrary to the common understanding and medical practice. This invention relates to a surprising finding that, in contrary to the common understanding and medical practices of using emulsions to deactivate an LA, this application discloses use of the emulsions to not only maintain the pharmacological effect of an LA, but also prolong its duration of action and reduce its toxicity.

This prolonged action of an emulsion of this invention is made possible by the onetime application by injection, infiltration and/or instillation of a relatively high dose of LA to provide a high concentration of LA in the local tissue of the application.

Subjects suffering from or susceptible to pain can benefit from alleviation of pain according to the methods described herein for 12 hours to 24 hours, 24 hours to 48 hours, 48 hours to 72 hours, or more. If longer period of pain relief is desired, the administration of the local anesthetic emulsion can be repeated. Typically, administration of the emulsion can be repeated two, three or more times within about 1 week or months.

The present methods for treating or preventing pain can further comprise co-administering another prophylactic or therapeutic agent, which includes, but is not limited to, an anti-infective agent, an anti-inflammatory agent, an anti-renal failure agent, and anti-cardiovascular disease agent, an antiemetic agent an anxiolytic agent, and an analgesic agent, or an antidote for reducing any potential side effect of the local anesthetic. Such potential side effects include, but are not limited to, nausea, vomiting, headache, low white blood cell count, low red blood cell count, low platelet count, headache, fever, lethargy, a muscle ache, general pain, bone pain, pain at an injection site, diarrhea, neuropathy, pruritus, a mouth sore, alopecia, anxiety or depression.

It is anticipated that one of the therapeutic benefits from the pain relief using the emulsions of this invention is to reduce the use of general anesthetics or patient self-controlled analgesia, especially the opiate or opioid drugs.

Despite of the relative high dose given in the onetime application, the emulsion of this invention does not produce a burst release of LA or a high LA $C_{max}$ exceeding the drug's cardiovascular or CNS level of toxicity. The release profile of LA from emulsion is smooth, flat, and peak-less.

The LA dose, emulsion volume, or application frequency (once or multiple times) can be determined by the drug efficacy as measured by the pain score such as NRS-R NRS-A and the reduction in use of general anesthetic drug (which may result in less cardiovascular and CNS toxicity) could be determined by studies of local and systemic pharmacokinetic profiles and/or in vitro release profiles.

Similarly the method of application (injection, infiltration or instillation or combination thereof) can be determined by drug efficacy as measured by the pain score such as NRS-R NRS-A or the reduction in use of general anesthetic drug (which may result in less cardiovascular and CNS toxicity) could be determined by studies of local and systemic pharmacokinetic profiles, or and/or in vitro release profiles.

It is a preferred method to administer a high volume of the emulsion of this invention for better efficacy as long as the LA $C_{max}$ remains below its cardiovascular and CNS toxicity level, the local tissue (e.g., surgical incision) is able to receive and accommodate such a high volume and the wound healing is not compromised.

The dose of the LA in an emulsion of this invention is also dependent on type of surgery or wound, the pain severity and co-administration of other anesthetics.

The duration of action is also dependent on the route of administration but it is generally anticipated that a single injection into a soft tissue of a large volume of the emulsion will provide a longer duration of action over many injections of a smaller volume (e.g., infiltration). Similarly, injection or infiltration into a deep tissue generally will provide a longer analgesic effect than topical application or instillation. Furthermore, an undiluted emulsion tends to provide a longer action than a diluted emulsion.

For a surgical incision or wound, a combination of infiltration and instillation is a common method of administration. For a given incision/wound, it is generally desired to apply the maximum emulsion volume by infiltration to cover the maximum tissue area. It is also desired to infiltrate the incision/wound and instill any remaining volume that the wound can hold. For nerve block, injection or infiltration is the preferred route of administration.

It is anticipated that the pain relief from the emulsions of this invention can be delivered by an amide LA such as but not limited to ropivacaine since all amide LAs share the similar physical, chemical and pharmacological properties.

Once the emulsion dose volume is determined, it can be administered over various time periods including, but not limited to, about every 12 hours, about every 24 hours, about every 36 hours, about every 48 hours, about every 72 hours, about every week, about every two weeks, about every three weeks, about every month, and about every two months.

The emulsion dose and dosing frequency can be adjusted in accordance with a variety of factors including type, age, weight, sex and medical condition of the subject; the severity of the condition to be treated; the route of administration; the renal or hepatic function of the subject; and the particular local anesthetic employed. A person skilled in the art can readily determine the effective amount of the local anesthetic useful for treating pain, including the specific type of pain to be treated.

The in vivo release property of a given emulsion of this invention can be evaluated by performing an in vitro release test, which is especially useful for ensuring that the emulsion of this invention retains its slow-release property after it has been modified. For example, an in vitro release test can be used to determine the extent of dilution that can be used to dilute an emulsion without losing its slow-release property.

The viscosity of the emulsion of this invention is also a consideration of selecting a route of administration or dilution. For instillation or topical application, the emulsion viscosity can be relatively high since the emulsion can be easily administered by extrusion using a syringe without a needle. For infiltration or injection, a lower viscosity is necessary for the emulsion, because it has to be injected through a needle using a syringe. Further, for nerve block application, the emulsion must be of even lower viscosity since a longer needle or catheter is usually needed for such application. The viscosity of the emulsion of this invention changes with water content or dilution ratio. A low ratio dilution (with little water) may result in viscosity too high to inject. Other the other hand, an exceedingly high dilution (with too much water) would cause the emulsion to lose its slow-release property. Therefore, the emulsion viscosity and in vitro release property can be balanced to define an acceptable diluent and dilution method for the emulsion of this invention.

The emulsion of this invention can be administered prior to, concurrently with, or after an opioid or non-opioid analgesic agent, or on the same day, or within 1 hour, 2 hours, 12 hours, 24 hours, 48 hours or 72 hours of each other.

In one embodiment, the emulsion of the present invention is a translucent, uniform liquid filled into a glass or plastic container such as a vial, bottle, ampule, syringe and bag. A typical volume per container is between 5 mL and 50 mL, preferably between 10 mL and 25 mL. The liquid is drawn into a syringe prior to use.

In a preferred embodiment, the emulsion of the present invention is provided in a pre-filled syringe with attached hypodermic needle attached and is ready for injection. This feature is particularly desirable for application during a surgery.

In one embodiment, the pre-filled syringe can also comprise a needle suitable for injection, installation and infiltration and topical application of the emulsion.

In one embodiment, the needle used for the emulsion is an 18-25 G needle, preferably a 21 G needle.

In a certain embodiment, the emulsion of the present invention is administered via injection or infiltration into a soft tissue or near a nerve using a needle attached to a syringe or a needle attached to a catheter and then a syringe.

In a certain embodiment, the emulsion of the present invention is infiltrated or applied to the open surgical wound either topically or injected with a syringe. In some embodiments, the formulations are administered by a subcutaneous, intradermal, intramuscular, or percutaneous injection.

In one embodiment, the emulsion will be administered via wound infiltration into the surgical site.

In one embodiment, the emulsion will be administered via wound instillation into the surgical site.

In one embodiment, the emulsion will be administered via a combination of wound infiltration and instillation into the surgical site. The range of administered volume will be dependent on surgical incision size and the location of the surgical incision. A typical volume is between 5 mL and 50 mL. A preferred administered volume is between 10 mL and 40 mL. A typical volume ratio between infiltration and instillation is 1:20 to 20:1. A typical syringe and needle combination is used to conduct the wound infiltration. The typical size of syringe is between 1 mL and 50 mL. A preferred size of syringe is between 10 mL and 30 mL. The typical size of needle is between 18-30 G, 3/8 to 3-1/2 inches. A preferred size of needle is between 19-22 G, 1 to 1-1/2 inches.

In another embodiment, the emulsion will be administered via regional nerve block, field block, plane block, peripheral nerve block near a specific nerve or bundle of nerves to block sensation of pain from a specific area to the body.

In one preferred embodiment, the emulsion will be administered via ultrasound-guided regional nerve block. A typical volume is between 5 mL and 50 mL. A preferred administration volume is between 10 mL and 40 mL. In another preferred embodiment, the emulsion will be administered using nerve block needle with or without tubing and extension set. A typical nerve block needle is between 20-22 G, with 1-3/8 to 6 inches. In one embodiment, the emulsion will be administered via epidural needle. A typical epidural needle is between 17-22 G.

Dilution is always desirable for a drug used for surgical pain control to allow for adjustment in dose volume, concentration and release profile since surgeries vary in incision size and degree of pain. Moreover, the nerve block application generally requires a lower LA concentration. It is known that some polymer-based extended-release formulations cannot be diluted therefore limiting their applicability in surgery. Being an oil-in-water emulsion, the composition of this invention is compatible with water and thus can be diluted. In a preferred embodiment, the emulsion of the present invention is diluted with water, saline, a dextrose solution or other injectable diluents that are safe to use before administering into a patient.

Dilution of the emulsion of this invention may change its viscosity and drug release profile. Therefore, the dilution can be made only in a defined range. A high viscosity (e.g., >400 centipoise) will make an injection through a needle difficult. The viscosity of an emulsion of this invention is sensitive to diluent and dilution ratio. A diluent for an emulsion of this invention may be water, saline, a dextrose solution, an IV infusion fluid such as Ringer's lactate solution or other injectable diluents that are safe to use such as ethanol or propylene glycol, or a combination thereof. A dilution ratio is defined as volume of the diluent-to-the volume of an emulsion. Surprisingly, dilution with water would initially increase the viscosity of the emulsion of the present invention and then subsequently decrease the viscosity after excessive dilution. For example, a 1:1 dilution with saline and 2:1 dilution with water increases the emulsion viscosity from about 500 to 17000-28000 and to approximately 40000 centipoise, respectively. On the other hand, excessive dilution (e.g., a dilution ratio >10:1) would cause an emulsion to change the slow LA release properties and compromise pain relief efficacy or duration of action. To balance the viscosity and release properties, the emulsion of this invention is diluted with a diluent at a dilution ratio between 10:1 and 1:1. A preferred dilution ratio for an emulsion of this invention is 4:1 to 2:1 with a saline or water. For example, a 2:1 dilution with Normal Saline resulted in an emulsion viscosity of about 21 centipoise while maintaining an acceptable in vitro release profile (EX 12, 13). Since a different diluent will also have different impact on the viscosity and is likely to require adjustment to the dilution ratio, a preferred dilution ratio for a new diluent is a ratio that will result in an emulsion viscosity of no more than 400 centipoise and an acceptable in vitro release profile for the LA.

In one embodiment, the emulsion is diluted with saline, then mixed to uniform consistency by a physical mixing action including but not limited to repeated withdrawing and expelling action using a syringe in an open container and shaking the emulsion and diluent in a closed container, e.g., in a bottle, vial, bag or syringe. A preferred container for mixing is an open sterile container for surgical bedside admix and a sterile syringe. A withdraw/expel cycle of 3-20 times will generate a uniformed mixture. A preferred repetition of 8-12 cycles has also generated uniformed mixture.

In one embodiment, the emulsion and its diluted emulsion have different in vitro release profiles. For example, an undiluted emulsion has a LA release range of 19-46% at 12 hours, 30-60% at 24 hours, 45-77% at 48 hours, 56-84% at 72 hours. The 2:1 saline diluted emulsion has a LA release range of 49-90% at 12 hours, 67-100% at 24 hours, 83-100% at 48 hours, 89-100% at 72 hours, using the in vitro release method as described in Example 13. In one embodiment, an emulsion of the present invention has a LA release range of 19-90% at 12 hours, 30-100% at 24 hours, 45-100% at 48 hours, 56-100% at 72 hours, preferably, a LA release range of 19-49%, at 12 hours, 30-67% at 24 hours, 45-83% at 48 hours, 56-89% at 72 hours.

Some liquid injectable drugs or implants are incompatible with suture or other surgical materials such as a mesh, therefore can't be used for a surgery where a suture or mesh is needed. In one embodiment, the emulsion of this invention is compatible with surgical materials such as mesh and suture and can be safely used in surgeries where mesh and suture are used. The typical mesh materials include polypropylene (PP), expanded polytetrafluoroethylene (e-PTFE), PP/PCG-25 (poliglecaprone 25). The typical suture materials include Nylon, polydioxanone, polypropylene, polyglyconate, polyglactin 910.

In one embodiment, a surgical mesh will retain 90-110% of its original tensile strength after being soaked in an emulsion of the present invention for at least 7 days at 37 deg C (Ex 6).

In one embodiment, a surgical suture will retain 90-110% of its original tensile strength after being soaked in an emulsion of the present invention at least 7 days at 37 deg C (Ex 6).

A good drug for administering to a surgical or wound site shall not affect the healing process of the incision or wound. Some drugs are known to change the wound healing process, thus changing the healing rate or scar formation after application. The emulsion of this invention has shown to be free of any deleterious effect on wound healing process as indicated by the unchanged tensile strength and scar-free appearance of the healed tissue from a surgical wound (Ex 2, 5). In one embodiment, the emulsion of this invention has no adverse impact on wound healing of a soft tissue. In another embodiment, the emulsion of this invention has no adverse impact on bone healing. In another embodiment, the emulsion of the invention has no adverse impact on nerve tissues, including but not limited to sciatic nerve, ventral spinal root/branch, and peripheral nerves in tissue nearby the wound site.

Surgical pain can last up to 3-5 days, therefore it is desirable for the effect of a pain drug to last up 3-5 days. The emulsion of this invention is designed to have a prolonged residence at the injection site and to release LA slowly to produce the local anesthetic effect on the incision/wound site or a nerve block. The slow-release property can be demonstrated by an extended pharmacokinetic profile compared to LA in a regular solution formulation (e.g. the NAROPIN®). For example, a subcutaneous injection of the emulsion in rats provided an extended-release pharmacokinetic profile with a $C_{max}$ of 576-4110 ng/mL, $T_{max}$ of 0.5-6 hours and $T_{1/2}$ of 7-35 hours. A subcutaneous injection of the emulsion to minipigs produced an extended-release pharmacokinetic profile with a $C_{max}$ of 339-1570 ng/mL, $T_{max}$ of 4.75-16.8 hours, and $T_{1/2}$ of 17-41 hours. Infiltration of emulsion into a wound in minipigs produces a $C_{max}$ of 392-1080 ng/mL, $T_{max}$ of 1.08-5.5 hours, and $T_{1/2}$ of 18.6-31.7 hours. In a human study, infiltrating the the emulsion into a surgical wounds resulted in a $C_{max}$ of 200-3000 ng/mL, $T_{max}$ of 1-40 hours, and $T_{1/2}$ of 10-40 hours.

In one embodiment, the an emulsion of this invention provides a longer pharmacokinetic profile, a lower $C_{max}$, a longer $T_{max}$ and $T_{1/2}$ compared to the same dose of LA in a regular solution formulation such as in NAROPIN®.

In one embodiment, the pharmacokinetic profile of an emulsion of this invention has a lower $C_{max}$, a longer $T_{max}$ and greater $T_{1/2}$ than that produced by a solution formulation of the same LA.

In one embodiment, an emulsion of this invention provides a pharmacokinetic profile with a $C_{max}$ which is about 10-100% of the $C_{max}$ produced by a solution formulation of the same LA.

In one embodiment, an emulsion of this invention provides a pharmacokinetic profile with a $T_{max}$ which is about 5-80 fold that of the $T_{max}$ produced by a solution formulation of the same LA.

In one embodiment, an emulsion of this invention provides a pharmacokinetic profile with a $T_{1/2}$ which is about 2-5 fold that of the $T_{1/2}$ produced by a solution formulation of the same LA.

The emulsion of this invention also provides a longer duration of analgesic effects compared to a solution LA formulation (e.g., NAROPIN®) or a liposome formulation of the LA drug bupivacaine (Exparel®) in animals and humans.

In one embodiment, the emulsion of this invention provides 3-4 fold longer analgesia compared to NAROPIN® or Exparel as measured by the delayed time to first opioid use in human, or delayed response in using pin-prick model in animals. In another embodiment, the present emulsion provides longer term analgesia and enhance recovery after surgery (ERAS) as measured by the shorter time spent in the PACU. (EX 3).

In one embodiment, the emulsion of this invention provides better analgesic efficacy for the management of postoperative pain when administered via wound infiltration or nerve block, compared to NAROPIN® (ropivacaine solution), Marcaine (bupivacaine solution), Exparel (a liposome formulation of bupivacaine), saline placebo, vehicle placebo in human, as measured by a lower pain intensity score, including but not limited to, a lower mean area under the curve (AUC) of the NRS-A and/or NRS-R pain intensity score through 0-24, 0-48, 0-72, 24-72, 24-48, 48-72 hours post dose. In another embodiment, it shows better analgesic efficacy measured by less total opioid consumption in oral morphine equivalent dose for the following post-administration time periods: 0-6, 0-12, 0-24, 0-48, 0-72, 6-12, 6-24, 6-48, 6-72, 12-24, 12-48, 12-72, 24-48, 24-72, 48-72. In another embodiment, the present emulsion provides better efficacy as measured by lower total opioid use through Day 7 and through the end of study/treatment. In another embodiment, this emulsion shows better efficacy by higher subject satisfaction with analgesia at 24, 48, 72 hours. In still another embodiment, it shows better efficacy by earlier time to discharge readiness including but not limited to the assessment based on the MPADSS at 12, 24, 48 and 72 hours. (EX 2).

In another embodiment, the emulsion of this invention provides a pain score at rest (NRS-R) or a pain score with activities (NRS-A) lower than that by NAROPIN®, Marcaine, Exparel, saline, vehicle placebo in human during post administration windows of 0-24h, 0-48h, 0-72h, 24-48h, 48-72h, and 24-72h, when administered via wound infiltration (EX 2).

In another embodiment, the administration of the emulsion of this invention via wound infiltration/instillation or nerve block reduces the opioid consumption by patients after the surgery. In a preferred embodiment, the administration of emulsion via wound infiltration/instillation or nerve block reduces the opioid consumption by the patients by no less than 5%, 10%, 20%, 30%, 40%, or 50%. In another preferred embodiment, the administration of emulsion via wound infiltration/instillation or nerve block reduces the opioid consumption by the patients compared to the administration of NAROPIN®, Marcaine®, or Exparel®.

In one embodiment, the emulsion of this invention does not cause local anesthetic systemic toxicity (LAST) when administered via wound infiltration or nerve block. In another preferred embodiment, the emulsion of this invention does not cause more local anesthetic systemic toxicity (LAST) when administered via wound infiltration or nerve block when comparing the same dose of the LA in NAROPIN®, Marcaine®, or Exparel®.

Use of an emulsion compositions for pain relief, comprising:
a. a local anesthetic,
b. an oil phase, and
c. an aqueous phase, wherein
  i. the local anesthetic is at a concentration up to 4% by weight of the emulsion,
  ii. the oil phase is at a concentration between about 20% and 99.8% by weight of the emulsion,
  iii. the oil phase comprises lecithin and vegetable oil at weight ratio between 7:1 and 2:5, and
  iv. the emulsion contains particles or droplets with about 30 to 2500 nanometers.

The disclosure provides, a method for relief of a pain in a subject in need thereof, the method comprising:
administering to the subject an effective amount of an emulsion composition, the emulsion composition comprising:
an amide local anesthetic, wherein the amide local anesthetic is no more than about 4% by weight of the emulsion;
an oil phase, the oil phase comprising lecithin and a vegetable oil at a weight ratio between 2:1 to 5:4, and wherein the oil phase is at a concentration between about 20% and 99.8% by weight of the emulsion; and
an aqueous phase, wherein the emulsion contains particles or droplets with a diameter between about 30 nm and about 2500 nm.

In certain aspects, the pain is a member selected from the group consisting of somatogenic, neurogenic, and psychogenic pain.

In certain aspects, the pain is post-operative pain or cancer pain.

In certain aspects, administration of the composition provides pain relief for at least 24 hours in the subject.

In certain aspects, the composition is administered to the subject by a member selected from the group consisting of wound infiltration, instillation, and nerve block.

In certain aspects, the amide local anesthetic is a member selected from the group consisting of bupivacaine, ropivacaine and pharmaceutically acceptable salts thereof.

In certain aspects, the amide local anesthetic is a ropivacaine.

In certain aspects, administering the ropivacaine composition by wound infiltration or instillation maintains a ropivacaine plasma level below its cardiotoxic level.

In certain aspects, the administration of the composition does not cause any detectable local anesthetic systemic toxicity (LAST).

In certain aspects, the vegetable oil is a member selected from the group consisting of sesame oil, soybean oil, olive oil and a combination thereof.

In certain aspects, the vegetable oil is sesame oil.

In certain aspects, wherein the composition further comprises a water-miscible organic solvent selected from a group consisting of ethanol, propylene glycol, glycerol and liquid polyethylene glycol.

In certain aspects, the composition has a viscosity between about 2 and 600 centipoise.

In certain aspects, the composition has a pH of between about 4 and about 7.

In certain aspects, wherein the composition is a translucent or white opaque liquid and is filterable through a 0.2-micron filter.

In certain aspects, the lecithin contains no less than 75% by weight phosphatidylcholine.

In certain aspects, the composition is diluted with saline to a 2:1 ratio or greater or with water to a 4:1 ratio or greater before administration.

In certain aspects, more than 90% by weight of the amide local anesthetic is non-covalently bound to the oil droplets.

In certain aspects, the composition is administered using a syringe, a syringe with a needle or a syringe with a catheter.

In certain aspects, administration of the composition provides a prolonged pharmacokinetic profile with a lower Cmax, longer Tmax and greater T½ compared to the same local anesthetic in a solution formulation.

In certain aspects, the composition provides pain relief by reducing the pain intensity as measured by a pain intensity scale by no less than 10% for up to 72 hours.

In certain aspects, administration of the composition provides a quick onset of relief in at least 60 minutes and lasts for about 48-72 hours after administration.

In certain aspects, the composition provides a delay in opioid use by the subject.

In certain aspects, the composition is provided in a vial or a syringe, ready-to-inject or ready-to-administer.

In certain aspects, the composition is administered via a syringe with a needle or a syringe with a catheter.

In certain aspects, the oil droplets are non-liposomal and substantially free of liposomal bilayer membrane structure.

The present invention will be further understood by reference to the following non-limiting examples.

EXAMPLE 1

Human Pharmacokinetic Study of a Ropivacaine Emulsion in Comparison with a Ropivacaine Solution (NAROPIN®)

In this example, a human pharmacokinetic (PK) study was performed for a ropivacaine emulsion of the present invention in a composition coded as F-53. F-53 comprises about 2.6% ropivacaine HCl, about 52% soy lecithin and about 35% sesame oil, about 0.02% EDTA sodium, about 0.1% cysteine and water. F-53 was injected and infiltrated at surgical incision sites to 12 human subjects at a 200 mg dose. Blood samples were collected and ropivacaine concentration in the blood was determined by LC-MS analysis. The PK results were compared to the PK data reported (Pettersson et al) for a ropivacaine solution (NAROPIN® Injection). NAROPIN® Injection is an FDA approved drug which is a sterile, isotonic solution that contains ropivacaine HCl, sodium chloride and water. The table below summarize the human PK data from F-53 and NAROPIN®.

| PK Parameters | 200 mg Ropivacaine in F-53 | 300 mg Ropivacaine in NAROPIN® |
|---|---|---|
| $T_{max}$, h | 10.1 (2.18-30.1) | 0.77 |
| $C_{max}$, ng/mL | 573 (224-1280) | 1500 |
| $AUC_{0-inf}$, ng h/mL | 20,400 (10,200-35,100) | 13,829 |
| $T_{1/2}$, h | 25.4 (16.3 -33.7) | 10.9 |

Conclusion: F-53 has a distinctive human PK profile with a greatly extended-release as evidenced by the longer $T_{max}$, longer $T_{1/2}$, and lower $C_{max}$ compared to the solution formulation NAROPIN®. The longer $T_{max}$ and $T_{1/2}$ indicated a prolonged anesthetic action and the lower $C_{max}$ a better safety profile since a high $C_{max}$ is related to cardiotoxicity.

EXAMPLE 2

Human Efficacy and Safety Study

In this example, a human clinical safety and efficacy study of a ropivacaine emulsion was conducted in human subject after mini-abdominoplasty. This was a randomized, double-blind, single-site study to evaluate the safety, PK profile, and analgesic duration of action of F-53 in men and women ≥18 and ≤70 years of age for the management of postoperative pain after mini-abdominoplasty surgery. Each randomly assigned patient received either F-53 (200 mg ropivacaine) or placebo (0.9% NaCl) administered into soft tissue by wound infiltration and instillation before closure after mini-abdominoplasty. The study revealed the following key findings:
1. F-53 effectively reduced the pain intensity (NRS-R) in patients by 10-25% in each 12-24 hour time period up to 72 hours
2. F-53 analgesic effect appeared quickly (onset within 60 min) and lasted evenly during the 0-72 hours after drug administration.
3. The F-53 treatment delayed time to the first use of opioids in patients: 16.5 hours in F-53 vs 12.3 hours in placebo.
4. F-53 was well tolerated and showed no evidence of local tissue reaction or impairment of wound healing. No subject was assessed as having LAST by the investigator. No serious adverse events (SAEs) were observed in the study. Clinical laboratory data and vital sign values did not reveal any abnormalities suggestive of a negative impact of F-53. No subject in F-53 group experienced a clinically significant ECG change.

EXAMPLE 3

Local Anesthetic Efficacy of Ropivacaine Emulsions in Comparison with NAROPIN® and Exparel® (1.3% Bupivacaine Liposome Injectable Suspension)

The purpose of this study was to compare the local anesthetic efficacy of the ropivacaine emulsions of the present invention, NAROPIN® Injection and Exparel® (1.3% bupivacaine liposome injectable suspension), which is a liposomal formulation of bupivacaine.

The local anesthetic efficacy of these formulations following subcutaneous injections was evaluated in the guinea pigs using a pin-prick model. This model involves injecting a formulation under the guinea pig's skin to form a wheal (a small swelling), pricking the wheal area with a pin and observing for animal's response. The local anesthetic activity is confirmed if the animal does not respond to the pinprick.

F-10, F-11 and F-13 are the emulsion formulations prepared according to the present invention, each containing ropivacaine (1% as HCl salt in F-10, 2% as HCl salt in F-11, or 2% as free base in F-13), about 52% soy lecithin and about 35% sesame oil, about 0.02% EDTA, about 0.1% cysteine, ethanol and water. Ropivacaine HCl and ropivacaine differ greatly from the ropivacaine freebase in hydrophobicity with the HCl salt having a log P of 1.1 and the free base having a log P of 2.9.

Figure 6:
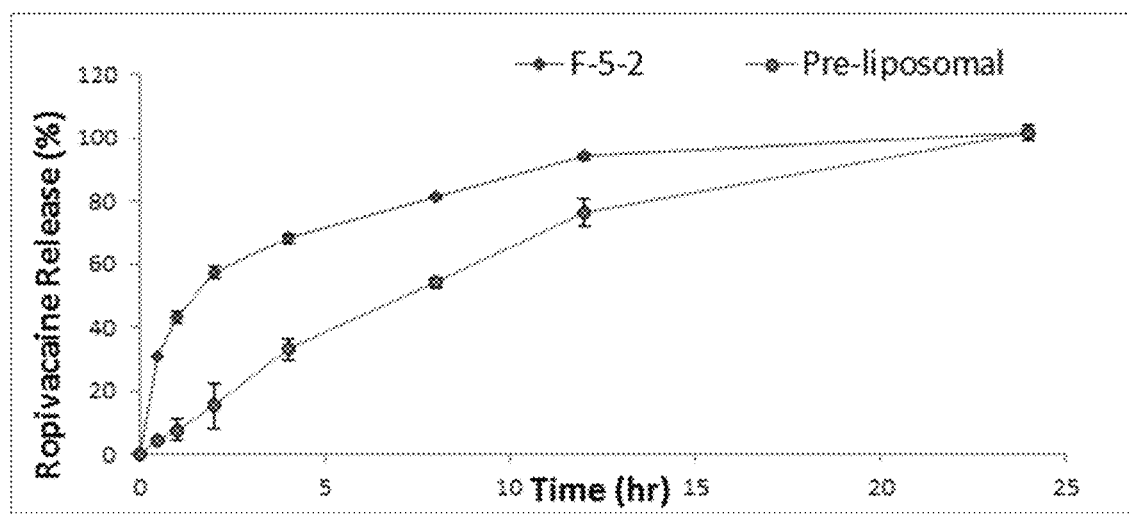
FIG. 6 illustrates prolonged local anethetic effect of a ropivacine emulsion as compared to a ropivacaine solutiuon (NAROPIN®) or a bupivacaine liposome drug (Exparel®).

For comparison, NAROPIN® formulation containing 1% ropivacaine HCl, a liposome formulation of bupivacaine (Exparel® containing 13.3 mg/mL bupivacaine) and V-10, which is the vehicle of F-10 (blank emulsion containing no drug) are also tested. For each formulation, a same dose (mg/kg) was given to six animals and the numbers of animals with no response (non-response) were plotted over time (FIG. 6).

All formulations except V-10 exhibited significant local anesthetic action. However, the duration of the local anesthetic action (time to maintain 50% non-response) varied greatly in the following order: F-11≈F-13 (12-13h)>F-10 (9h)>Exparel® (5h)>NAROPIN® (3h). No obvious adverse reaction was observed in the test animals.

Conclusion: an emulsion of the present invention containing either a salt or free base of a local anesthetic drug cannot only maintain the local anesthetic activities, but also provide the desired prolonged local anesthetic efficacy. The emulsion of the present invention exhibited much longer duration of action than the solution formulation NAROPIN® and the liposome formulation Exparel®. Clearly, the emulsion formulations of this invention do not share the same efficacy as the solution or liposome formulation. Moreover, the emulsion formulation of this invention is capable of providing the prolonged local anesthetic activity regardless the hydrophobicity of the LA.

EXAMPLE 4

Safety Assessment of a Ropivacaine Emulsion

The purpose of this study was to measure the maximum tolerated dose (MTD) and local toxicity at the injection site of a ropivacaine emulsion (F-32, which has a similar composition as the F-53 in Example 1) in Sprague-Dawley (SD) rats by a single subcutaneous injection. For comparison, NAROPIN® injection was also tested. The study details are summarized in the table below:

| | | Animal Death | |
|---|---|---|---|
| Test Article | Dose Level (mg/kg) | Male | Female |
| F-32 vehicle | 0 | 0/5 | 0/5 |
| NAROPIN® | 44 | 3/5 | 3/5 |
| | 88 | 8/8 | 1/1 |
| F-32 | 50 | 0/5 | 0/5 |
| | 200 | 0/5 | 0/5 |
| | 400 | 0/5 | 0/5 |

Mortalities were observed in animals administered with NAROPIN® at doses of 44 mg/kg or 88 mg/kg on Day 1. The clinical observations in the NAROPIN® treated animals included abnormal gait, rapid breathing, prostrate posture, salivation, convulsions, decreased activity/lethargy, hunched posture and loss of righting reflex. No mortality was observed in any of the F-32 treated animals. At 50 mg/kg, there were no toxicity findings (systemically or locally at the injection site) in the animals. Clinical observations of abnormal gait, activity decreased/lethargy, breathing difficulty, material around mouth and nose (red) were only observed at 400 mg/kg during Day 2 to 3.

Conclusion: F-32 is a much safer formulation than NAROPIN®. The MTD is less than 44 mg/kg for NAROPIN® and greater than 400 mg/kg for F-32.

EXAMPLE 5

Emulsion Impact on Wound Healing

In this example, the effect of a ropivacaine emulsion formulation (F-53) on wound healing was evaluated after wound infiltration/instillation into surgical incisions made on the back skin of minipigs. The incision was allowed to heal and the incision sites porcine skin was collected at 28 days after the dosing and cut into small samples for tensile test according to ASTM D638. Samples were pulled apart at a consistent rate until a break or separation occurred and the tensile strength [MPa] was recorded and compared between emulsion treated skin vs saline treated skin. On Day 28, the tensile breaking strengths are also similar comparing saline infiltrated skin (2.3 MPa +/−0.5 [Male], 4.8+/−1.3 [Female]) with emulsion infiltrated skin (3.0 MPa +/−0.7 [Male], 3.5+/−0.5 [female]), and no scar was observed in either group.

In conclusion, ropivacaine emulsion had no adverse impact on wound healing.

EXAMPLE 6

Emulsion Compatibility with Sutures and Mesh

In this example, the compatibility of a ropivacaine emulsion formulation (F-53) with sutures and mesh were evaluated in vitro.

Each suture tested in this study was cut into 13" length and soaked in F-53 or Normal Saline at 37° C. for 7 days. The breaking force was measured by tensile test per ASTM D2256.

Four types of sutures were tested (PDS II, Prolene, Maxon, Vicryl). For all suture tested, the F-53 soaked samples exhibited the same breaking forces as the comparable Normal saline-soaked control after up to 7 days of soaking, indicating that the F-53 has the same mechanical effect on the sutures as Normal Saline and all sutures exposed to F-53 for up to 7 days demonstrated no significant decrease of tensile strength after the prolonged exposure to F-53.

For mesh testing, each mesh sample was cut into 0.5"× 1.5" strips along its length with the 1.5" dimension being the longitudinal direction. The strips were submerged (soaked) in F-53 or Normal Saline for 7 days in at 37° C. Three types of mesh were tested (Bard Dulex, Prolene, Ultrapro). Each strip sample was measured by tensile test per ASTM D5035.

The breaking forces for Bard Dulex and Prolene appeared unaltered with the soaking in either F-53 or Normal Saline, whereas the UltraPro mesh exhibited a slight decrease of breaking force after being in contact with either F-53 or Normal saline. F-53 and Normal Saline showed similar effect on the mechanical integrity of the tested mesh.

In conclusion, the emulsion of this invention is compatible with sutures or meshes.

EXAMPLE 7

In Vitro Release of a Ropivacaine Emulsion

In this example, the in vitro release profile of a ropivacaine emulsion formulation was measured and compared to the pre-liposomal formulation prepared according to the composition and process described in the Example 1 and 2 of U.S. Pat. No.: 9,849,088 B2. The ropivacaine emulsion formulation was prepared using the emulsion process as described in Example 18 while the pre-liposomal was prepared using the process described in Example 1 and 2 of U.S. Pat. No.: 9,849,088 B2. The final compositions are summarized in the Table below:

| Component name | (% w/w | |
|---|---|---|
| | Emulsion | Pre-liposomal |
| Ropivacaine HCl monohydrate | 2.55 | 4.78 |
| Soy lecithin | 52 | 53.9 |
| EDTA disodium dihydrate | 0.02 | No |
| Ethanol | 8 | 6 |
| Sesame Oil | 36 | No |
| Castor Oil | No | 35.2 |
| L-cysteine | 0.1 | 0.1 |
| Water added in the process | Yes | No |

Figure 5:
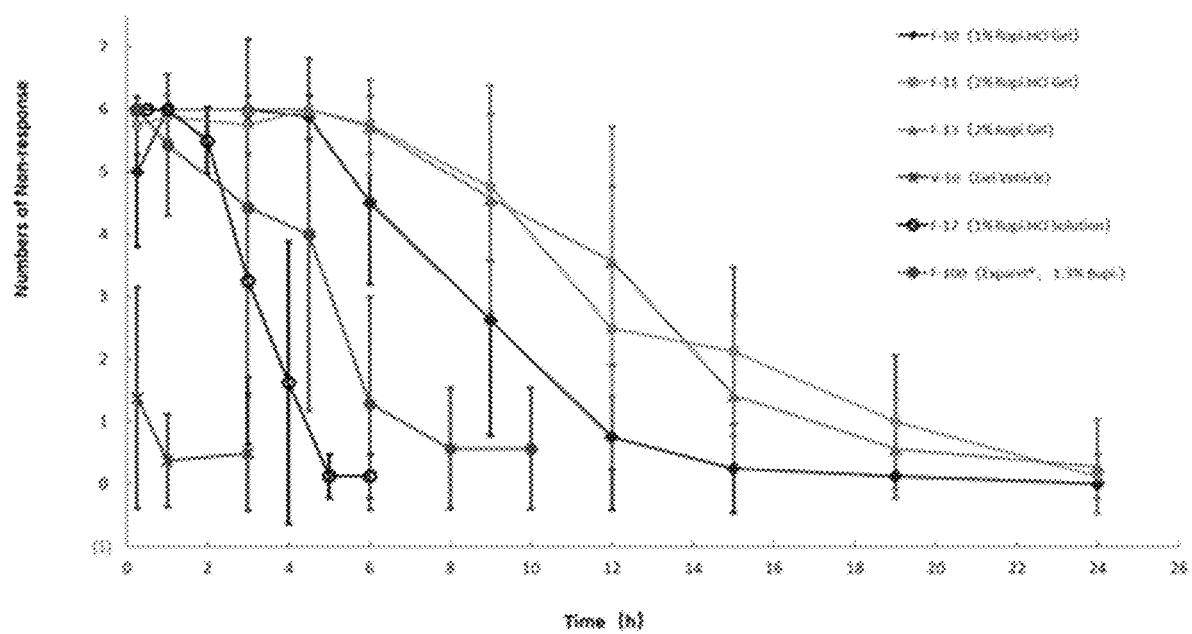
FIG. 5 illustrates in vitro release of a ropivacaine emulsion of the current invention as compared to a ropivacaine liposome composition prepared according to Ex 1 & 2 in U.S. Pat. No. 10,206,876B2

A USP type 4 dissolution apparatus was used to measure the in vitro release of ropivacaine from the emulsion (coded as F-5-2) and the pre-liposomal formulation. FIG. 5 provides the in vitro release profile comparison.

Conclusion: The emulsion of the present invention exhibited a very different ropivacaine release profile from that by the pre-liposomal formulation, even though pre-liposomal formulation has similar components. Compared to the pre-liposomal formulation, the emulsion has a faster release rate within the first 2 hours and a slower rate after that. Clearly, the emulsion is not bioequivalent to the pre-liposomal formulation even though the pre-liposomal formulation was made from similar components

EXAMPLE 8

Stability of a Ropivacaine Emulsion

In this example, long-term stability data of a ropivacaine emulsion in a composition as described in Example 1 are provided in the following tables:
Stability at 2-8° C.

| Test | Specifications | Initial | 3 months | 6 months | 9 months | 12 months | 18 months | 24 month |
|---|---|---|---|---|---|---|---|---|
| Appearance | Translucent liquid | Pass | Pass | Pass | Pass | Pass | Pass | Pass |
| Ropivacaine Assay | 90.0-110.0% Label Claimed | 103.5% | 106.0% | 104.0% | 103.0% | 103.5% | 100.8% | 107.8% |
| Ropivacaine N-Oxide | NMT 0.2% | 0% | 0% | 0% | 0% | 0% | 0% | 0.03% |

-continued

| Test | Specifications | Initial | 3 months | 6 months | 9 months | 12 months | 18 months | 24 month |
|---|---|---|---|---|---|---|---|---|
| Ropivacaine Related Compound A | NMT 0.01% | 0% | 0% | 0% | 0% | 0% | 0% | 0% |
| Total Impurities | NMT 0.2% | 0% | 0% | 0% | 0.04% | 0% | 0.02% | 0.03% |
| Viscosity | Report Result | 561.6 cP | 537.6 cP | 544.8 cP | 544.8 cP | 570.0 cP | 578.4 cP | 303.5 cP |

Stability at 25° C.

| Test | Specifications | Initial | 4 months | 6 months | 12 months | 18 months | 24 months |
|---|---|---|---|---|---|---|---|
| Appearance | Translucent liquid | Pass | Pass | Pass | Pass | Pass | Pass |
| Ropivacaine Assay | 90.0-110.0% Label Claim | 103.5% | 105.5% | 104.5% | 103.0% | 100.9% | 105.3% |
| Ropivacaine N-Oxide | NMT 0.2% | 0% | 0% | 0% | 0% | 0% | 0.01% |
| Ropivacaine Related Compound A | NMT 0.01% | 0% | 0% | 0% | 0% | 0% | 0% |
| Total Impurities | NMT 0.2% | 0% | 0% | 0% | 0% | 0.05% | 0.01% |
| Viscosity | Report Result | 561.6 cP | 546.0 cP | 549.6 cP | 571.2 cP | 576.0 cP | 342.7 cP |

Conclusion: The emulsion of the present invention is stable at 2-8° C. and 25° C. for 24 months. Specifically, the emulsion is capable of keeping the ropivacaine assay between 90 and 110% of the label claim, the N-Oxide to below 0.2%, the ropivacaine Related Compound A below 0.01% and the total impurity to below 0.2% after 24 months at 2-8° C. and 25° C.

EXAMPLE 9

Particle Size Analysis of a Ropivacaine Emulsion

In this example, the particle size of a ropivacaine emulsion in the same composition as described in Example 1 are measured under different conditions. A dynamic light scattering spectrometer (Malvern Zetasizer Model Nano) was used to measure the average particle size (reported as Z-average in diameter) of the emulsion droplets before and after dilution with water. The particle size varies with the water dilution ratio and preparation method, however, the measured particle size remained consistent by the same sample preparation method.

| Measurement | Sample preparation method | Z-average (nm) |
|---|---|---|
| 1 | Undiluted | 209 |
| 2 | 2 g emulsion + 10 mL water, handshake 2 min | 2504 |
|  | Repeat | 2547 |
|  | Repeat | 2190 |
| 3 | 0.15 g emulsion + 10 mL water, vortex 2 min | 825 |
| 4 | 0.15 g emulsion + 10 mL water, vortex 10 min | 593 |
| 5 | 0.15 g emulsion + 10 mL water, vortex 10 min and sonicate 10 min | 487 |
| 6 | 0.15 g emulsion + 10 mL water, vortex 2 min and sonicate 60 min | 412 |
| 7 | 0.3 g emulsion + 10 mL water, vortex 2 min and sonicate 150 min | 389 |
| 8 | 0.5 g emulsion + 10 mL water, vortex 5 min and sonicate 90 min | 444 |
|  | Repeat | 543 |
|  | Repeat | 356 |
| 9 | 0.5 g emulsion + 10 mL water, handshake and sonicate 30 min | 213 |
|  | Repeat | 219 |
|  | Repeat | 218 |
|  | Repeat | 217 |

Conclusion: The emulsion of the present invention has Z-average particle size of 209 nm undiluted. When diluted with water, its particle size ranged from about 213 nm to 2504 nm.

EXAMPLE 10

Electron Microscope Imaging of a Ropivacaine Emulsion

In this example, microscopic structure of the ropivacaine emulsion in the same composition as described in Example 1 was examined using a transmission electron microscope (TEM) using a Talos 120L TEM and a negative stain method. For comparison, a well-known liposome drug (Ambisome®) was also imaged.

The TEM images are shown in FIG. 4. Each particle/droplet present in the emulsion of this invention has a solid core (i.e., without the empty internal void) and has no distinctive membrane, whereas a liposome particle has an empty core and is surrounded by the distinctive bilayer lipid membrane.

Conclusion: an undiluted emulsion of the present invention contains visible particles between about 30 nm and 500 nm, and diluted emulsion contains visible particles 30-2500 nm, consistent with the dynamic light scattering finding in Example 9.

EXAMPLE 11

Injectability of a Ropivacaine Emulsion

In this example, the injectability of the ropivacaine emulsion in the same composition as described in Example 1 was measured. The injectability is defined as the time needed to expel 10 mL of the emulsion through a hypodermic needle using a 10 mL plastic syringe.

The injection time was measured as the time required to extrude 10 mL of a liquid filled in the 10 mL syringe through the attached needle or catheter at a force at about or no greater than 25 Newtons. An injection force of 25 Newtons is considered acceptable by most medical practitioners. A typical injection force is measured to be 20-30 N fhttp://www.sciencedirect.com/science/article/pii/S1098733903005741?via%3Dihub) and an injection time of 5-10 min and an 18-25G needle are considered acceptable ("TAP in Laparoscopic Sleeve Gastrectomy." https://videos.exparel.com/video-playlist/19). The table below provides the injection time recorded for a ropivacaine emulsion when it was undiluted or diluted with water or ethanol.

| Formulation | Needle size (Gauge and length) | Injection Time for 10 mL (min) |
|---|---|---|
| Ropivacaine emulsion, undiluted | 18G × 1" | 0.5 |
| | 19G × 1" | 1.5 |
| | 21G × 1½" | 2 |
| | 25G × ⅝" | 4.3 |
| Ropivacaine emulsion, diluted 2× with normal saline | 18G × 1" | <0.16 |
| | 19G × 1" | <0.16 |
| | 21G × 1½" | 0.16 |
| | 25G × ⅝" | 0.33 |
| | 27G × 1/2" | 2 |
| | 22G × 2" Catheter | 0.5 |
| Ropivacaine emulsion, diluted with ethanol (added to about 4% of the emulsion weight) | 18G × 1" | 0.25 |
| | 19G × 1" | 0.5 |
| | 21G × 1½" | 1.6 |
| | 25G × ⅝" | 6.5 |
| | 22G × 2" Catheter | 0.92 |

Conclusion: Ten (10) milliliters of the ropivacaine emulsion can be injected through an 18-27G needle or a 22G catheter from a 10 mL plastic syringe using 25 Newtons of force in less than 7 minutes.

EXAMPLE 12

Viscosity of Ropivacaine Emulsion Upon Dilution

In this example, a ropivacaine emulsion (F-53) was diluted at different ratios with water or normal saline and the viscosity of the diluted emulsions measured:

| Dilution ratio (Diluent vol: F53 vol) | Viscosity (CPs) | Acceptable for Injection |
|---|---|---|
| F-53 undiluted | 581 | Yes |
| Saline: F-53 = 1:1 | 27813 | No with a needle, but yes without a needle |
| Saline: F-53 = 2:1 | 21 | Yes |
| Saline: F-53 = 4:1 | 4 | Yes |
| Water: F-53 = 2:1 | 40605 | No with a needle, but yes without a needle |
| Water: F-53 = 4:1 | 387 | Yes |

Conclusion: an emulsion of this invention can be diluted in saline at a ratio of 2:1 or greater or in water at a ratio of 4:1 or greater and still maintaining its injectability.

EXAMPLE 13

In Vitro Release from a Diluted Emulsion

In this example, a ropivacaine emulsion (F-53) was diluted in saline at 2:1 ratio (viscosity=21 centipoise) and its in vitro release profile was determined. The in vitro release method involved a USP dissolution apparatus with dialysis membrane.

| | Ropivacaine release (%) | | | | | | | | |
|---|---|---|---|---|---|---|---|---|---|
| Time (h) | 0.5 | 2 | 6 | 12 | 24 | 48 | 72 | 96 | 120 | 144 |
| Saline: F-53 = 2:1 | 9 | 18 | 34 | 49 | 67 | 83 | 89 | 92 | 97 | 99 |
| F-53 undiluted | 2 | 5 | 12 | 19 | 30 | 45 | 56 | 65 | 72 | 81 |

Conclusion: a diluted emulsion of this invention maintains a slow release profile (about 3 days) as the undiluted emulsion while improving the emulsion injectability mentioned in Example 12.

EXAMPLE 14

Effect of pH on Stability of a Ropivacaine Emulsion

In this example, the stability of the ropivacaine in the emulsion in the same composition as described in Example 1 was examined as function of the emulsion pH. Multiple samples were prepared having different pH levels in the same base ropivacaine emulsion composition. Each sample was heat stressed at 121° for 60 mins. Impurities growth after heating is summarized in the table below:

| Emulsion pH | Impurity growth (%) |
|---|---|
| 3 | 1.00 |
| 3.5 | 0.80 |
| 4 | 0.50 |
| 4.5 | 0.60 |
| pH 4.5 (pH not adjusted) | 0.60 |
| 5 | 0.60 |
| 5.5 | 0.60 |
| 6 | 0.40 |
| 6.5 | 0.50 |
| 7 | 0.30 (cloudy) |

Conclusion: The best chemical stability was observed at an emulsion pH between pH 4 and pH 7. However, at pH 7, the emulsion appeared to be less physically stable.

EXAMPLE 15

Effect of Water on Stability of a Ropivacaine Emulsion

In this example, the physical stability of ropivacaine in the emulsion in the same composition as described in Example 1 was examined as function of water level in emulsion. Multiple samples were prepared to have different water content using the same base ropivacaine emulsion composition. Each sample was stored at 2-8° C., 25° C. and 40° C. and observed for appearance over time. The finding is summarized in the table below:

| Water level in emulsion (% wt) | Storage temperature (° C.) | Observation |
|---|---|---|
| 0.3 | 2-8 | Initially translucent, no change for 1.5 years |
| 0.75 | | Initially translucent, no change for 1.5 years |
| 1.0 | | Initially translucent, no change for 1.5 years |
| 0.3 | 25 | Initially translucent, no change for 1.5 years |
| 0.75 | | Initially translucent, no change for 1.5 years |
| 1.0 | | Turned hazy at 25 days |
| 0.3 | 40 | Initially translucent, no change for 1.5 years |
| 0.75 | | Turned hazy at 25 days |
| 1.0 | | Turned hazy at 25 days |

Conclusion: The best physical stability was observed with 0.3% water content. However, all three water levels are acceptable since the haziness is not correlated to loss of assay or purity.

EXAMPLE 16

Optimal Antioxidant(s) for a Ropivacaine Emulsion

In this example, the effect of EDTA and cysteine on stability of the ropivacaine emulsion in the same composition as in Example 1 was studied. Multiple lots of emulsions in the same base composition were made with different concentrations of EDTA and L-cysteine. The emulsions were stored at 25° C. and 40° C. to study the growth of impurities, in particular, ropivacaine N-oxide. Table below summarizes the finding:

| Emulsion Lot # | EDTA disodium added (w/w %) | Cysteine added (w/w %) | Total Impurities at Initial (%) | Total Impurities after 1 month at 25° C. (%) | Total Impurities after 1 month at 40° C. (%) | N-Oxide at Initial (%) | N-Oxide (after 1 month at 25° C. (%) | N-Oxide after 1 month at 40° C. (%) |
|---|---|---|---|---|---|---|---|---|
| 20201116 | 0 | 0 | 0.05 | 0.18 | 0.28 | 0.01 | 0.02 | 0.01 |
| 20201124 | 0.02 | 0 | 0.03 | 0.09 | 0.16 | 0 | 0.03 | 0.08 |
| 20201016 | 0.04 | 0 | 0.09 | 0.09 | 0.60 | 0.01 | 0.04 | 0.22 |
| 20201120 | 0 | 0.1 | 0.09 | 0.03 | 0.34 | 0 | 0 | 0 |
| 20201020 | 0 | 0.2 | 0.05 | 0 | 0.12 | 0 | 0 | 0 |
| 20201207 | 0.02 | 0.1 | 0 | 0 | 0.44 | 0 | 0 | 0 |
| 20201130 | 0.02 | 0.1 | 0.03 | 0.02 | 0.27 | 0 | 0.02 | 0 |
| 20201103 | 0.02 | 0.1 | 0.04 | 0 | 0.39 | 0.01 | 0 | 0 |
| 20200104 | 0.02 | 0.2 | 0 | 0.01 | 0.02 | 0 | 0 | 0 |
| 20201027 | 0.04 | 0.2 | 0.02 | 0 | 0.11 | 0 | 0 | 0 |
| 20201222 | 0.04 | 0.1 | 0.02 | 0 | 0 | 0 | 0 | 0 |

Conclusion: Without an antioxidant, the ropivacaine emulsion formed various impurities including the N-Oxide. When only EDTA sodium (0.02% or 0.04%) or only cysteine (0.1% or 0.2%) was added to the ropivacaine emulsion, the N-oxide ceased to form but other impurities continued to grow. When BOTH the EDTA sodium (0.02% or 0.04%) and cysteine (0.1% or 0.2%) were added, the growth of all impurities including the N-oxide was inhibited. Therefore, a combination of EDTA sodium (0.02% or 0.04%) and cysteine (0.1% or 0.2%) is the preferred antioxidant for the emulsion of the present invention.

In a subsequent study, an additional antioxidant was also added to the same ropivacaine emulsion containing the EDTA sodium and cysteine combination (0.02%+0.1%) as follow:

| % w/w | F-11 | F19 | F20 | F21 | F22 | F23 | F24 | F25 | F26 | F27 | F28 | F29 |
|---|---|---|---|---|---|---|---|---|---|---|---|---|
| Carbon dioxide gas | Headspace | | | | | | | | | | | |
| Edetic acid | | 0.02 | | | | | | | | | | |
| Tocopherol | | | 0.02 | | | | | | | | | |
| BHA | | | | 0.03 | | | | | | | | |
| BHT | | | | | 0.03 | | | | | | | |

-continued

| % w/w | F-11 | F19 | F20 | F21 | F22 | F23 | F24 | F25 | F26 | F27 | F28 | F29 |
|---|---|---|---|---|---|---|---|---|---|---|---|---|
| Ascorbyl palmitate | | | | | 0.02 | | | | | | | |
| Ascorbic acid | | | | | | 1.0 | | | | | | |
| Methionine | | | | | | | 0.3 | | | | | |
| Proline | | | | | | | | | 0.34 | | | |
| Phenol | | | | | | | | | | 0.45 | | |
| Glutathione | | | | | | | | | | | 0.5 | |
| Tromethamine | | | | | | | | | | | | 0.6 |

Each sample was sealed in a glass vial. One F-11 vial was filled with carbon dioxide gas in the vial headspace before sealing. All vials were heated at 121° C. for 2 hours. Impurity content was measured before and after the heating by HPLC. The levels of N-oxide are shown in the table below:

| | F-11 + air headspace | F11 + CO$_2$ in headspace | F19 | F20 | F21 | F22 | F23 | F24 | F25 | F26 | F27 | F28 | F29 |
|---|---|---|---|---|---|---|---|---|---|---|---|---|---|
| Before heating | | | | | | 0.0 | | | | | | | |
| After heating | 0.16 | 0.00 | 0.18 | 0.46 | 0.34 | 0.17 | 0.14 | 0.10 | 0.13 | 0.14 | 0.26 | 0.13 | 0.16 |
| pH | 6.06 | 6.06 | 6.03 | 6.03 | 6.17 | 6.06 | 5.92 | 5.93 | 6.17 | 6.14 | 6.12 | 5.98 | 6.44 |

Conclusion: additional antioxidants including CO$_2$ gas, ascorbyl palmitate, ascorbic acid, methionine and glutathione can further inhibit the N-oxide growth under heat. Among them, CO$_2$ gas provided the most significant improvement to the ropivacaine stability.

EXAMPLE 17

Particle Size and Distribution in the Undiluted Emulsion

In this example, the emulsion was measure by dynamic light scattering (DLS) to determine the particle size and polydispersity index (PDI) using a Malvern Zetasizer.

| Emulsion Vial# | Measurement# | Z-Average (d.nm) | PDI | D(v.0.5) | D(v.0.9) |
|---|---|---|---|---|---|
| 1 | 1 | 74.55 | 1.000 | 50.8 | 65.9 |
|  | 2 | 90.67 | 1.000 | 55.4 | 73.3 |
| 2 | 1 | 288.60 | 1.000 | 66.1 | 89.5 |
|  | 2 | 212.20 | 1.000 | 76.6 | 104.0 |
| 3 | 1 | 41.08 | 0.239 | 39.4 | 54.8 |
|  | 2 | 273.00 | 1.000 | 90.8 | 119.0 |
| 4 | 1 | 54.90 | 0.600 | 8.8 | 11.1 |
|  | 2 | 118.40 | 1.000 | 81.8 | 108.0 |
|  | AVG | 144 |  | 59 | 78 |
|  | STDEV | 99 |  | 26 | 35 |

The Z average is reported in nanometers (nm) and is defined as the "intensity weighted mean hydrodynamic size of the ensemble collection of particles measured by DLS". The polydispersity Index (PDI) is a measure size heterogeneity of the detected particles. A value greater than 0.7 indicate that the sample has a very broad size distribution.

D(v.0.5) is the volume median diameter D(v,0.5) which is the diameter where 50% of the distribution is above and 50% is below. Similarly, D(v,0.9) is the diameter where 90% of the volume distribution is below this value Conclusion: The emulsion of this invention is a polydisperse system that has a very broad size distribution with particles of size greater and smaller than 100 nm in diameter.

EXAMPLE 18

Process for Preparing the Emulsion

Step 1. Preparation of Oil Phase and Aqueous API Solution

Add oil and lecithin to a stainless-steel compounding vessel. Mix until a smooth, uniform and particle-free paste is formed ("Oil Phase").

Dissolve an LA (ropivacaine HCl) and other excipients such as antioxidant in water. Mix to obtain a clear solution ("Aqueous Phase").

Step 2. Preparation of an Oil-in-water Emulsion

Combine the Oil and Aqueous Phases. Mix with a high shear homogenizer to form an oil-in-water. Continue the mixing until the mean emulsion droplet size is between 100 and 400 nm.

Step 3. Water Removal

Remove the excess water in the emulsion by vacuum drying to obtain an oil-in-water emulsion, an emulsion of both oil-in-water and water-in-oil types, or water-in-oil type emulsion, depending upon the final water content.

Step 4. Dilution or viscosity adjustment
As needed, adjust the water content or add a viscosity reducer (e.g., alcohol) to adjust the viscosity of the emulsion.

Step 5. Sterile Filtration and Filling
Pass the emulsion through a sterile filter to sterilize the emulsion and fill and seal the filtered emulsion aseptically into glass vials or syringes.

Modifications and variations of the present invention will be obvious to those skilled in the art from the foregoing detailed description and are intended to fall within the scope of the following claims. The teachings of all references cited herein are specifically incorporated by reference.

What is claimed is:

1. A method for relief of a pain in a subject in need thereof, the method comprising:
   administering to the subject an effective amount of a water-in-oil emulsion composition, comprising:
   an amide local anesthetic, which is ropivacaine, a pharmaceutically acceptable salt thereof or a combination thereof, wherein the amide local anesthetic is no more than about 4% by weight of the emulsion;
   an oil phase, the oil phase comprising lecithin and a vegetable oil at a weight ratio between 2:1 to 5:4; and
   a water-miscible organic solvent between 6% and 10% of the emulsion weight;
   an aqueous phase, where the water content is less than 5% of the emulsion weight, wherein small water droplets are dispersed in the oil phase and
   the emulsion contains particles or water droplets with a diameter between about 30 nm and about 500 nm.

2. The method of claim 1, wherein the vegetable oil is a member selected from the group consisting of sesame oil, soybean oil, olive oil and a combination thereof.

3. The method of claim 2, wherein the vegetable oil which is sesame oil.

4. The method of claim 1, wherein the lecithin is a member selected from the group consisting of LIPOID S75, LIPOID S 100, LIPOID E80, Phospholipond 90G and a combination thereof.

5. The method of claim 1, wherein the lecithin contains no less than 75% by weight phosphatidylcholine.

6. The method of claim 1, wherein the water-miscible organic solvent selected from a group consisting of ethanol, propylene glycol, glycerol and liquid polyethylene glycol.

7. The method of claim 1, wherein the composition has a viscosity between about 2 and about 40,000 centipoises.

8. The method of claim 1, wherein the composition is a translucent or white opaque liquid and is filterable through a 0.2-micron filter.

9. The method of claim 1, wherein more than 90% by weight of the amide local anesthetic is non-covalently bound to the oil droplets.

10. The method of claim 1, wherein the oil droplets or particles in the emulsion are non-liposomal and substantially free of liposomal bilayer membrane structure.

11. The method of claim 1, wherein the composition is diluted with saline to a 2:1 ratio or greater, which represents volume of diluent-to-the volume of emulsion, or with water to a 4:1 ratio or greater before administration.

12. The method of claim 1, wherein the composition is administered to the subject by a member selected from the group consisting of wound infiltration, instillation, and nerve block.

13. The method of claim 1, wherein the composition is administered using a syringe, a syringe with a needle or a syringe with a catheter.

14. The method of claim 1, wherein the composition is provided in a vial or a syringe, ready-to-inject or ready-to-administer.

15. The method of claim 1, wherein administration of the composition provides a prolonged pharmacokinetic profile with a lower $C_{max}$, longer $T_{max}$ and greater $T_{1/2}$ compared to the same local anesthetic in a solution formulation.

16. The method of claim 1, wherein administering the ropivacaine composition by wound infiltration or instillation maintains a ropivacaine plasma level below its cardiotoxic level.

17. The method of claim 1, wherein the administration of the composition does not cause any detectable local anesthetic systemic toxicity (LAST).

18. The method of claim 1, wherein the pain is a member selected from the group consisting of somatogenic, neurogenic, and psychogenic pain.

19. The method of claim 1, wherein the pain is post-operative pain or cancer pain.

20. The method of claim 1, wherein administration of the composition provides pain relief for at least 24 hours in the subject.

21. The method of claim 1, wherein the composition provides pain relief by reducing the pain intensity as measured by a pain intensity scale by no less than 10% for up to 72 hours.

22. The method of claim 1, wherein administration of the composition provides a quick onset of relief within 60 minutes and lasts for about 48-72 hours after administration.

23. The method of claim 1, wherein the composition provides a delay or reduction in opioid use by the subject.

24. The method of claim 1, wherein the emulsion composition comprises about 30% to about 40% vegetable oil by weight of the emulsion.

25. The method of claim 1, wherein the emulsion composition comprises about 50% to about 60% lecithin by weight of the emulsion.

26. The method of claim 1, wherein the emulsion composition comprises:
   about 2.55% w/w ropivacaine HCl monohydrate;
   about 52% w/w soy lecithin;
   about 0.02% w/w EDTA disodium dihydrate;
   about 8% w/w ethanol;
   about 36% w/w sesame oil; and
   about 0.1% w/w L-cysteine.

* * * * *